US010150774B2

(12) United States Patent
Li et al.

(10) Patent No.: US 10,150,774 B2
(45) Date of Patent: Dec. 11, 2018

(54) COMPOUNDS AND METHODS

(71) Applicant: INTRA-CELLULAR THERAPIES, INC., New York, NY (US)

(72) Inventors: Peng Li, New Milford, NJ (US); Hailin Zheng, Teaneck, NJ (US); Jun Zhao, Highland Park, NJ (US); Lawrence Wennogle, Hillsborough, NJ (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 0 days.

(21) Appl. No.: 15/512,005

(22) PCT Filed: Sep. 17, 2015

(86) PCT No.: PCT/US2015/050814
§ 371 (c)(1),
(2) Date: Mar. 16, 2017

(87) PCT Pub. No.: WO2016/044667
PCT Pub. Date: Mar. 24, 2016

(65) Prior Publication Data
US 2017/0291904 A1  Oct. 12, 2017

Related U.S. Application Data

(60) Provisional application No. 62/051,735, filed on Sep. 17, 2014, provisional application No. 62/052,283, filed on Sep. 18, 2014.

(51) Int. Cl.
*C07D 487/14* (2006.01)

(52) U.S. Cl.
CPC .................. *C07D 487/14* (2013.01)

(58) Field of Classification Search
CPC .......................... A61K 31/519; C07D 487/41
See application file for complete search history.

(56) References Cited

U.S. PATENT DOCUMENTS

| | | |
|---|---|---|
| 5,202,328 A | 4/1993 | de Laszlo et al. |
| 5,294,612 A | 3/1994 | Bacon et al. |
| 5,393,755 A | 2/1995 | Neustadt et al. |
| 5,824,683 A | 10/1998 | McKittrick et al. |
| 5,849,770 A | 12/1998 | Head et al. |
| 5,939,419 A | 8/1999 | Tulshian et al. |
| 5,962,492 A | 10/1999 | Warrellow et al. |
| 6,013,621 A | 1/2000 | Nishi et al. |
| 6,133,273 A | 10/2000 | Gilbert et al. |
| 6,235,742 B1 | 5/2001 | Bell et al. |
| 6,235,746 B1 | 5/2001 | Davis et al. |
| 6,316,444 B1 | 11/2001 | Hunt et al. |
| 6,423,716 B1 | 7/2002 | Matsuno et al. |
| 6,492,371 B2 | 12/2002 | Roylance |
| 6,498,165 B1 | 12/2002 | Armstrong et al. |
| 6,552,029 B1 | 4/2003 | Davis et al. |
| 6,586,423 B2 | 7/2003 | Bilodeau et al. |
| 6,599,908 B1 | 7/2003 | Davis et al. |
| 6,649,608 B2 | 11/2003 | Pease et al. |
| 6,670,368 B1 | 12/2003 | Breault et al. |
| 6,693,099 B2 | 2/2004 | Degenhardt et al. |
| 6,756,373 B1 | 6/2004 | Allerton et al. |
| 6,969,719 B2 | 11/2005 | Asberom et al. |
| 7,153,824 B2 | 12/2006 | Palmer et al. |
| 7,157,451 B2 | 1/2007 | Atwal et al. |
| 8,273,750 B2 | 9/2012 | Li et al. |
| 8,273,751 B2 | 9/2012 | Li et al. |
| 8,536,159 B2 | 9/2013 | Li et al. |
| 8,633,180 B2 | 1/2014 | Li et al. |
| 8,664,207 B2 | 3/2014 | Li et al. |
| 8,697,710 B2 | 4/2014 | Li et al. |
| 8,829,008 B2 | 9/2014 | Li |
| 9,000,001 B2 | 4/2015 | Li et al. |
| 9,073,936 B2 * | 7/2015 | Li ........................ C07D 487/14 |
| 9,157,906 B2 | 10/2015 | Greengard et al. |
| 2003/0069246 A1 | 4/2003 | Darrow et al. |
| 2003/0092908 A1 | 5/2003 | Pitts et al. |
| 2003/0162782 A1 | 8/2003 | Grossman et al. |
| 2004/0087517 A1 | 5/2004 | Burnet et al. |
| 2004/0259792 A1 | 12/2004 | Palmer et al. |
| 2005/0075795 A1 | 4/2005 | Pandit |
| 2005/0113379 A1 | 5/2005 | Ge et al. |

(Continued)

FOREIGN PATENT DOCUMENTS

| | | |
|---|---|---|
| DE | 19931206 A1 | 1/2001 |
| EP | 0 063 381 A1 | 10/1982 |

(Continued)

OTHER PUBLICATIONS

Ahn, H. et al., "Potent Tetracyclic Guanine Inhibitors of PDE1 and PDE5 Cyclic Guanosine Monophosphate Phosphodiesterases with Oral Antihypertensive Activity," Journal of Medicinal Chemistry, 1997, 40 (14), 2196-2210.
Al-Afaleq, E. et al., "Heterocyclic o-Aminonitriles: Preparation of Pyrazolo[3,4-d]-pyrimidines with Modification of the Substituents at the 1-Position," Molecules, 2001, 6, 621-638.
"Anxiety," [retrieved on May 14, 2008]. Retrieved online via Internet, URL: http://www.nlm.nih.gov/medlineplus/anxiety.html, 5 pages.
Aswar, M. et al., "Anti-Cataleptic Activity of Various Extracts of *Ocimum sanctum*," International Journal of Pharmaceutical Research and Development, 2010, 2 (6), 7 pages.
"Autism," [retrieved on May 14, 2008]. Retrieved online via Internet, URL: http://www.nlm.nih.gov/medlineplus/autism.html, 6 pages.

(Continued)

*Primary Examiner* — Erich A Leeser
(74) *Attorney, Agent, or Firm* — Hoxie & Associates, LLC

(57) ABSTRACT

The subject matter generally relates to compounds and methods of treatment and/or prophylaxis of CNS diseases, disorders, and/or injuries. In one aspect, the subject matter relates to inhibitors of phosphodiesterase 1 (PDE1) as neuroprotective agents and/or neural regenerative agents. In a further aspect, the subject matter relates to individuals that are at risk for the development of CNS disease or disorder.

28 Claims, No Drawings

(56) References Cited

U.S. PATENT DOCUMENTS

| | | |
|---|---|---|
| 2006/0252790 A1 | 11/2006 | Allen et al. |
| 2008/0176961 A1 | 7/2008 | Greengard et al. |
| 2008/0188492 A1 | 8/2008 | Li et al. |
| 2008/0193964 A1 | 8/2008 | Greengard et al. |
| 2008/0194592 A1 | 8/2008 | Mates et al. |
| 2010/0087450 A1 | 4/2010 | Mates et al. |
| 2010/0173878 A1 | 7/2010 | Li et al. |
| 2010/0273753 A1 | 10/2010 | Li et al. |
| 2010/0273754 A1 | 10/2010 | Li |
| 2010/0323997 A1 | 12/2010 | Fienberg et al. |
| 2011/0237561 A1 | 9/2011 | Li et al. |
| 2011/0245214 A1 | 10/2011 | Li et al. |
| 2011/0281832 A1 | 11/2011 | Li et al. |
| 2011/0312978 A1 | 12/2011 | Davis et al. |
| 2012/0053190 A1 | 3/2012 | Fienberg et al. |
| 2012/0071450 A1 | 3/2012 | Li et al. |
| 2012/0094966 A1 | 4/2012 | Li et al. |
| 2012/0136013 A1 | 5/2012 | Li et al. |
| 2012/0201754 A1 | 8/2012 | Li |
| 2012/0238589 A1 | 9/2012 | Li et al. |
| 2013/0018063 A1 | 1/2013 | Li et al. |
| 2013/0085123 A1 | 4/2013 | Li et al. |
| 2013/0239234 A1 | 9/2013 | Greengard et al. |
| 2013/0324565 A1 | 12/2013 | Li et al. |
| 2013/0331363 A1 | 12/2013 | Li et al. |
| 2013/0338124 A1 | 12/2013 | Li et al. |
| 2014/0005155 A1 | 1/2014 | Li et al. |
| 2014/0011783 A1 | 1/2014 | Li et al. |
| 2014/0148421 A1 | 5/2014 | Li et al. |
| 2014/0194396 A1 | 7/2014 | Li et al. |
| 2014/0315868 A1 | 10/2014 | Li et al. |
| 2014/0357606 A1 | 12/2014 | Li |
| 2015/0038474 A1 | 2/2015 | Li et al. |
| 2015/0072965 A1 | 3/2015 | Li et al. |
| 2015/0080357 A1 | 3/2015 | Li et al. |
| 2015/0197528 A1 | 7/2015 | Li et al. |
| 2015/0259353 A1 | 9/2015 | Li et al. |
| 2016/0031895 A1* | 2/2016 | Li .................. C07D 487/14 514/171 |
| 2016/0039835 A1 | 2/2016 | Li et al. |
| 2016/0083390 A1 | 3/2016 | Li et al. |
| 2017/0231994 A1 | 8/2017 | Li et al. |

FOREIGN PATENT DOCUMENTS

| | | |
|---|---|---|
| EP | 0 095 289 A2 | 11/1983 |
| EP | 0 201 188 A2 | 12/1986 |
| EP | 0 636 626 A1 | 2/1995 |
| EP | 0 911 333 A1 | 4/1999 |
| JP | 53031694 A | 3/1978 |
| KR | 10-1991-0006866 | 9/1991 |
| WO | WO 91/19717 A1 | 12/1991 |
| WO | WO 94/19351 A1 | 9/1994 |
| WO | WO 98/46606 A1 | 10/1998 |
| WO | WO 98/52568 A1 | 11/1998 |
| WO | WO 01/27113 A2 | 4/2001 |
| WO | WO 02/074312 A1 | 9/2002 |
| WO | WO 03/002567 A1 | 1/2003 |
| WO | WO 03/020702 A2 | 3/2003 |
| WO | WO 03/020724 A1 | 3/2003 |
| WO | WO 03/042216 A1 | 5/2003 |
| WO | WO 2006/133261 * | 12/2006 ........... A61K 31/519 |
| WO | WO 2006/133261 A2 | 12/2006 |
| WO | WO 2007/143568 A1 | 12/2007 |
| WO | WO 2007/143705 A2 | 12/2007 |
| WO | WO 2008/063505 A1 | 5/2008 |
| WO | WO 2008/070095 A1 | 6/2008 |
| WO | WO 2009/073210 A1 | 6/2009 |
| WO | WO 2009/075784 A1 | 6/2009 |
| WO | WO 2010/065148 A1 | 6/2010 |
| WO | WO 2010/065149 A1 | 6/2010 |
| WO | WO 2010/065151 A1 | 6/2010 |
| WO | WO 2011/043816 A1 | 4/2011 |
| WO | WO 2011/153129 A1 | 12/2011 |
| WO | WO 2011/153135 A1 | 12/2011 |
| WO | WO 2011/153136 A1 | 12/2011 |
| WO | WO 2011/153138 A1 | 12/2011 |
| WO | WO 2012/171016 A1 | 12/2012 |
| WO | WO 2013/192556 A2 | 12/2013 |
| WO | WO 2014/151409 A1 | 9/2014 |
| WO | WO 2016/022893 A1 | 2/2016 |
| WO | WO 2016/044667 A1 | 3/2016 |

OTHER PUBLICATIONS

Banker, Gilbert S. et al., Eds., Modern Pharmaceutics, Third Edition, Marcel Dekker Inc., New York, 1996.

Bastia, E. et al., "Effect of $A_1$ and $A_{2A}$ Adenosine Receptor Ligands in Mouse Acute Models of Pain," Neuroscience Letters, 2002, 328, 241-244.

Bender, A. et al., "Cyclic Nucleotide Phosphodiesterases: Molecular Regulation to Clinical Use," Pharmacological Reviews, 2006, 58 (3), 488-520.

Blokland, A. et al., "PDE Inhibition and Cognition Enhancement," 2012, 22 (4), 349-354 (abstract only).

Boyd, K. et al., "Dopamine Receptor Signaling and Current and Future Antipsychotic Drugs" in Current Antipsychotics, Handbook of Experimental Pharmacology, 212, Gross, G. et al., Eds., doi:10.1007/978-3-642-25761-2_3, Springer-Verlag, Berlin, 2012, pp. 53-86.

Burnouf, C. et al., "Synthesis, Structure-Activity Relationships, and Pharmacological Profile of 9-Amino-4-oxo-1-phenyl-3,4,6,7-tetrahydro[1,4]diazepino[6,7,1-hi]indoles: Discovery of Potent, Selective Phosphodiesterase Type 4 Inhibitors," Journal of Medicinal Chemistry, 2000, 43 (25), 4850-4867.

Chalimoniuk, M. et al., "Upregulation of Guanylyl Cyclase Expression and Activity in Striatum of MPTP-induced Parkinsonism in Mice," Biochemical and Biophysical Research Communications, 2004, 324, 118-126.

Chebib, M. et al., "1-Phenylpyrazolo[3,4-d]pyrimidines; Structure-Activity Relationships for C6 Substituents at $A_1$ and $A_{2A}$ Adenosine Receptors," Bioorganic & Medicinal Chemistry, 2000, 8, 2581-2590.

Chen, M. et al., "Effects of Bimatoprost 0.03% on Ocular Hemodynamics in Normal Tension Glaucoma," Journal of Ocular Pharmacology and Therapeutics, 2006, 22 (3), 188-193.

Chermat, R. et al., "Adaptation of the Tail Suspension Test to the Rat," Journal de Pharmacologie (Paris), 1986, 17 (3), 348-350.

Deshmukh, R. et al., "Amelioration of Intracerebroventricular Streptozotocin Induced Cognitive Dysfunction and Oxidative Stress by Vinpocetine—A PDE1 Inhibitor," European Journal of Pharmacology, 2009, 620 (1-3), 49-56.

Dewald, H. et al., "Synthesis and Potential Antipsychotic Activity of 1H-Imidazo[1,2-c]pyrazolo[3,4-e]pyrimidines," Journal of Medicinal Chemistry, 1988, 31, 454-461.

Ehrman, L. et al., "Phosphodiesterase 1B Differentially Modulates the Effects of Methamphetamine on Locomotor Activity and Spatial Learning Through DARPP32-Dependent Pathways: Evidence from PDE1B-DARPP32 Double-Knockout Mice," Genes, Brain and Behavior, 2006, 5 (7), 540-551.

Ennaceur, A. et al., "A New One-Trial Test for Neurobiological Studies of Memory in Rats. 1:Behavioral Data," Behavioral Brain Research, 1998, 31, 47-59.

Fienberg, A. et al., "DARPP-32: Regulator of the Efficacy of Dopaminergic Neurotransmission," Science, 1998, 281, 838-842.

Filgueiras, C. et al., "Phosphodiesterase Type 1 Inhibition Improves Learning in Rats Exposed to Alcohol During the Third Trimester Equivalent of Human Gestation," Neuroscience Letters, 2010, 473 (3), 202-207.

Gelbin, M. et al., "Ketene-S,N-acetals as Synthons for Heterocycles, New Synthesis of Pyrimidinones," Journal Für Praktische Chemie, 1987, 329 (5), 753-766.

Goodman & Gilman, Las bases farmacológicas de la terapéutica (The Pharmacological Basis of Therapeutics), McGraw-Hill Interamericana, 2007, p. 892, cited within text of Opposition to Letters Patent in Costa Rican Patent Application No. 2011-0313, 7 pages.

(56) References Cited

OTHER PUBLICATIONS

Greengard, P. et al., "Beyond the Dopamine Receptor: The DARPP-32/Protein Phosphatase-1 Cascade," Neuron, 1999, 23, 435-447.
Han, P. et al., "The Calcium/Calmodulin-dependent Phosphodiesterase PDE1C Down-regulates Glucose-induced Insulin Secretion," The Journal of Biological Chemistry, 1999, 274 (32), 22337-22344.
Hulley, P. et al., "Cyclic AMP Promotes the Survival of Dopaminergic Neurons in vitro and Protects Them from the Toxic Effects of MPP+," Journal of Neural Transmission [Supplemental], 1995, 46, 217-228.
International Search Report of International Application No. PCT/US2015/050814, dated Dec. 18, 2015, 2 pages.
Japanese Patent Office, Patent Abstracts of Japan, Abstract for JP 53031694 A, Date of publication of application Mar. 25, 1978, 1 page.
Jiang, M. et al., "Chemoenzymatic Asymmetric Total Synthesis of Phosphodiesterase Inhibitors: Preparation of a Polycyclic Pyrazolo[3,4-d]pyrimidine from an Acylnitroso Diels-Alder Cycloadduct-Derived Aminocyclopentenol," Journal of Organic Chemistry, 2005, 70, 2824-2827.
Kakkar, R. et al., "Inhibition of Bovine Brain Calmodulin-Dependent Cyclic Nucleotide Phosphodiesterase Isozymes by Deprenyl," Life Sciences, 1996, 59 (21), 337-341.
Kakkar, R. et al. "Amantadine: An Antiparkinsonian Agent Inhibits Bovine Brain 60 kDa Calmodulin-Dependent Cyclic Nucleotide Phosphodiesterase Isozyme," Brain Research, 1997, 749 (2), 290-294.
Kakkar, R. et al. "Calmodulin-dependent Cyclic Nucleotide Phosphodiesterase (PDE1)," CMLS Cellular and Molecular Life Sciences, 1999, 55 (8-9), 1164-1186.
Klaissle, P. et al., "Physical Activity and Environmental Enrichment Regulate the Generation of Neural Precursors in the Adult Mouse Substantia Nigra in a Dopamine-dependent Manner," BMC Neuroscience, 2012, 13, 132, doi:10.1186/1471-2202-13-132, 15 pages.
Kleppisch, T., "Phosphodiesterases in the Central Nervous System" in cGMP: Generators, Effectors and Therapeutic Implications, Handbook of Experimental Pharmacology, 191, Schmidt, H. et al., Eds., Springer-Verlag, Berlin, 2009, pp. 71-92.
Laddha, S. et al., "A New Therapeutic Approach in Parkinson's Disease: Some Novel Quinazoline Derivatives as Dual Selective Phosphodiesterase 1 Inhibitors and Anti-inflammatory Agents" Bioorganic & Medicinal Chemistry, 2009, 17 (19), 6796-6802.
Lundqvist, T. et al., "Exploitation of Structural and Regulatory Diversity in Glutamate Racemases," Nature, 2007, 447, 817-822.
Mani, S. et al., "Requirement for DARPP-32 in Progesterone Facilitated Sexual Receptivity in Female Rats and Mice," Science, 2000, 287, 1053-1056.
Medina, A., "Therapeutic Utility of Phosphodiesterase Type 1 Inhibitors in Neurological Conditions," Frontiers in Neuroscience, 2011, 5, 21, 6 pages.
Murray, F. et al., "Expression and Activity of cAMP Phosphodiesterase Isoforms in Pulmonary Artery Smooth Muscle Cells from Patients with Pulmonary Hypertension: Role for PDE1," American Journal of Physiology, Lung Cellular and Molecular Physiology, 2007, 292, L294-L303.
Murray, T. et al., "LY503430, A Novel α-Amino-3-hydroxy-5-methylisoxazole-4-propionic Acid Receptor Potentiator with Functional, Neuroprotective and Neurotrophic Effects in Rodent Models of Parkinson's Disease," The Journal of Pharmacology and Experimental Therapeutics, 2003, 306 (2), 752-762.
Nishi, A. et al., "Advanced Research on Dopamine Signaling to Develop Drugs for the Treatment of Mental Disorders: Biochemical and Behavioral Profiles of Phosphodiesterase Inhibition in Dopaminergic Neurotransmission," Journal of Pharmacological Sciences, 2010, 114, 6-16.
Noguchi, M. et al., "A Facile Preparation of 7-(Substituted Amino-)-6H-pyrrolo[3,4-d]-pyrimidine Derivatives," Bulletin of the Chemical Society of Japan, 1989, 62 (9), 3043-3045.
Pardo, C. et al., "Synthesis of 1-(p-Nitrobenzyl)Azoles and 1-(p-Nitrobenzyl)Benzazoles," OPPI Briefs, 2000, 32 (4), 385-390.

Park, E, et al., "Traumatic Brain Injury: Can the Consequences Be Stopped?" CMAJ, 2008, 178 (9), 1163-1170.
Polli, J. et al., "Expression of a Calmodulin-dependent Phosphodiesterase Isoform (PDE1B1) Correlates With Brain Regions Having Extensive Dopaminergic Innervation," The Journal of Neuroscience, 1994, 14 (3), 1251-1261.
Porsolt, R. et al., "Depression: A New Animal Model Sensitive to Antidepressant Treatments," Nature, 1977, 266, 730-732.
Poulsen, S. et al., "High-Pressure Synthesis of Enantiomerically Pure C-6 Substituted Pyrazolo[3,4-d]pyrimidines," Bioorganic & Medicinal Chemistry Letters, 2001, 11, 191-193.
Prickaerts, J. et al., "Possible Role of Nitric Oxide-Cyclic GMP Pathway in Object Recognition Memory: Effects of 7-Nitroindazole and Zaprinast," European Journal of Pharmacology, 1997, 337, 125-136.
Reed, T. et al., "Phosphodiesterase 1B Knock-Out Mice Exhibit Exaggerated Locomotor Hyperactivity and DARPP-32 Phosphorylation in Response to Dopamine Agonists and Display Impaired Spatial Learning," The Journal of Neuroscience, 2002, 22 (12), 5188-5197.
Rybalkin, S. et al., "Cyclic GMP Phosphodiesterases and Regulation of Smooth Muscle Function," Circulation Research, 2003, 93, 280-291.
Schmidt, C., "Phosphodiesterase Inhibitors as Potential Cognition Enhancing Agents," Current Topics in Medicinal Chemistry, 2010, 10 (2), 222-230.
Sharma, R. et al., "Regulation of Calmodulin-Stimulated Cyclic Nucleotide Phosphodiesterase (PDE1): Review," International Journal of Molecular Medicine, 2006, 18, 95-105.
Shimizu, K. et al., "Calmodulin-Dependent Cyclic Nucleotide Phosphodiesterase (PDE1) is a Pharmacological Target of Differentiation-Inducing Factor-1, an Antitumor Agent Isolated from *Dictyostelium*," Cancer Research, 2004, 64, 2568-2571.
Shook, B. et al., "Design and Characterization of Optimized Adenosine $A_{2A}/A_1$ Receptor Antagonists for the Treatment of Parkinson's Disease," Journal of Medicinal Chemistry, doi:10.1021/jm201640m, 2012, 47 pages.
Turko, I. et al., "Inhibition of Cyclic GMP-Binding Cyclic GMP-Specific Phosphodiesterase (Type 5) by Sildenafil and Related Compounds," Molecular Pharmacology, 1999, 56, 124-130.
Ungerstedt, U. et al., "Quantitative Recording of Rotational Behavior in Rats After 6-Hydroxy-dopamine Lesions of the Nigrostriatal Dopamine System," Brain Research, 1970, 24, 485-493.
Ungerstedt, U., "Stereotaxic Mapping of the Monoamine Pathways in the Rat Brain," Acta Physiologica Scandinavica, Supplementum 367, 1971, 1-48.
Vatter, S. et al., "Differential Phosphodiesterase Expression and Cytosolic $Ca^{2+}$ in Human CNS Tumour Cells and in Non-Malignant and Malignant Cells of Rat Origin," Journal of Neurochemistry, 2005, 93, 321-329.
Wolff, M. Ed., Burger's Medicinal Chemistry and Drug Discovery, Fifth Edition, vol. I: Principles and Practice, John Wiley & Sons, New York, 1995, 975-977.
Xia, Y. et al., "Synthesis and Evaluation of Polycyclic Pyrazolo[3,4-d]pyrimidines as PDE1 and PDE5 cGMP Phosphodiesterase Inhibitors," Journal of Medicinal Chemistry, 1997, 40, 4372-4377.
Youdim et al., "The Path from Anti Parkinson Drug Selegiline and Rasagiline to Multi-functional Neuroprotective Anti Alzheimer Drugs Ladostigil and M30," Current Alzheimer Research, 2006, 3, 541-550.
Ghorab, M. et al., "Synthesis, Anticancer and Radioprotective Activities of Some New Pyrazolo[3,4-d]pyrimidines Containing Amino Acid Moieties," Arzneimittelforschung, 2009, 59 (2), 96-103.
International Search Report for International Application No. PCT/US2014/025666 dated Jul. 7, 2014, 3 pages.
International Search Report for International Application No. PCT/US2006/022066 dated Apr. 3, 2007, 1 page.
Patani, G. et al., "Bioisosterism: A Rational Approach in Drug Design," Chemical Reviews, 1996, 96 (8), 3147-3716.
Takimoto, E., "Controlling Myocyte cGMP, Phosphodiesterase 1 Joins the Fray," Circulation Research, 2009, 105, 956-964.

\* cited by examiner

COMPOUNDS AND METHODS

CROSS REFERENCE TO RELATED APPLICATIONS

This application is a United States Application under 35 U.S.C. § 371 claiming benefit of PCT Application No. PCT/US2015/050814, filed on Sep. 17, 2015, which claims the benefit of earlier filed United States provisional applications U.S. 62/051,735, filed Sep. 17, 2014, and U.S. 62/052,283, filed Sep. 18, 2014, each of which is incorporated herein by reference in their entireties.

FIELD OF THE INVENTION

The field generally relates to compounds and methods of treatment and/or prophylaxis of central nervous system (CNS) diseases, disorders, and/or injuries. In one aspect, the field relates to inhibitors of phosphodiesterase 1 (PDE1) as neuroprotective agents and/or neural regenerative agents. In a further aspect, the field relates to preventing the development of a CNS disease or disorder in an individual at risk for the development of a CNS disease or disorder.

BACKGROUND OF THE INVENTION

Cyclic nucleotide phosphodiesterases (PDEs) downregulate intracellular cAMP and cGMP signaling by hydrolyzing these cyclic nucleotides to their respective 5'-monophosphates (5'AMP and 5'GMP). Eleven families of phosphodiesterases have been identified, but only PDEs in Family I, the $Ca^{2+}$/calmodulin-dependent phosphodiesterases (CaM-PDEs), which are activated by $Ca^{2+}$-calmodulin, have been shown to mediate the calcium and cyclic nucleotide (e.g. cAMP and cGMP) signaling pathways. The three known CaM-PDE genes, PDE1A, PDE1B, and PDE1C, are all expressed in central nervous system tissue. PDE1A is expressed throughout the brain with higher levels of expression in the CA1 to CA3 layers of the hippocampus and cerebellum and at a lower level in the striatum. PDE1A is also expressed in the lung and heart. PDE1B is predominately expressed in the striatum, dentate gyrus, olfactory tract and cerebellum, and its expression correlates with brain regions having high levels of dopaminergic innervation. Although PDE1B is primarily expressed in the central nervous system, it is also detected in the heart, is present in neutrophils and has been shown to be involved in inflammatory responses of this cell. PDE1C is expressed in olfactory epithelium, cerebellar granule cells, striatum, heart, and vascular smooth muscle.

CaM-PDEs play a critical role in mediating signal transduction in brain cells, particularly within an area of the brain known as the basal ganglia or striatum. For example, NMDA-type glutamate receptor activation and/or dopamine D2 receptor activation result in increased intracellular calcium concentrations, leading to activation of effectors such as calmodulin-dependent kinase II (CaMKII) and calcineurin and to activation of CaM-PDEs, resulting in reduced cAMP and cGMP. Dopamine D1 receptor activation, on the other hand, leads to activation of adenylate cyclases, resulting in increased cAMP. This cyclic nucleotide in turn activates protein kinase A (PKA; cAMP-dependent protein kinase). Production of cGMP is known to occur in tissues involved in cognitive function through various stimulations such as nitric oxide production induced by high intracellular calcium levels and to subsequently activate protein kinase G (PKG; cGMP-dependent protein kinase). PKG and PKA phosphorylate downstream signal transduction pathway elements such as DARPP-32 (dopamine and cAMP-regulated phosphoprotein) and cAMP responsive element binding protein (CREB). Phosphorylated DARPP-32 in turn inhibits the activity of protein phosphates-1 (PP-1), thereby increasing the state of phosphorylation of substrate proteins such as progesterone receptor (PR), leading to induction of physiologic responses. D1 receptor signaling is disrupted in schizophrenia, contributing to cognitive impairment in the disease. The role of cAMP and cGMP in cognitive function has been well established in animal studies. Studies in rodents also have suggested that inducing cAMP and cGMP synthesis through activation of dopamine D1 or progesterone receptor enhances progesterone signaling associated with various physiological responses, including the lordosis response associated with receptivity to mating in some rodents. See Mani, et al., Science (2000) 287: 1053, the contents of which are incorporated herein by reference.

CaM-PDEs can therefore affect dopamine-regulated and other intracellular signaling pathways in the basal ganglia (striatum), including but not limited to nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), DARPP-32, and endorphin intracellular signaling pathways.

Phosphodiesterase (PDE) activity, in particular, phosphodiesterase 1 (PDE1) activity, functions in brain tissue as a regulator of locomotor activity and learning and memory. PDE1 is a therapeutic target for regulation of intracellular signaling pathways, preferably in the nervous system, including but not limited to a dopamine D1 receptor, dopamine D2 receptor, nitric oxide, noradrenergic, neurotensin, CCK, VIP, serotonin, glutamate (e.g., NMDA receptor, AMPA receptor), GABA, acetylcholine, adenosine (e.g., A2A receptor), cannabinoid receptor, natriuretic peptide (e.g., ANP, BNP, CNP), endorphin intracellular signaling pathway and progesterone signaling pathway. For example, inhibition of PDE1B should act to potentiate the effect of a dopamine D1 agonist by protecting cGMP and cAMP from degradation, and should similarly inhibit dopamine D2 receptor signaling pathways, by inhibiting PDE1 activity that is a consequence of D2 receptor-mediated increases in intra-cellular calcium. Chronic elevation in intracellular calcium levels is linked to cell death in numerous disorders, particularly in neurodegenerative diseases such as Alzheimer's, Parkinson's and Huntington's Diseases and in disorders of the circulatory system leading to stroke and myocardial infarction. PDE1 inhibitors are therefore potentially useful in diseases characterized by reduced dopamine D1 receptor signaling activity, such as Parkinson's disease, restless leg syndrome, depression, narcolepsy and cognitive impairment such as cognitive impairment associated with schizophrenia. PDE1 inhibitors are also useful in diseases that may be alleviated by the enhancement of progesterone-signaling such as female sexual dysfunction.

Additionally, neurogenesis is a vital process in the brains of animals and humans, whereby new nerve cells are continuously generated throughout the life span of the organism. The newly formed cells are able to differentiate into functional cells of the central nervous system and integrate into existing neural circuits in the brain. Neurogenesis is known to persist throughout adulthood in two regions of the mammalian brain: the subventricular zone (SVZ) of the lateral ventricles and the dentate gyrus of the hippocampus. In these regions, multipotent neural progenitor cells (NPCs) continue to divide and give rise to new functional neurons and glial cells. It has been shown that a variety of factors can stimulate adult hippocampal neurogenesis, e.g., adrenalectomy, voluntary exercise, enriched environment, hippocampus dependent learning and antidepressants. Other factors, such as adrenal hormones, stress, age and drugs of abuse negatively influence neurogenesis.

While the importance of neurogenesis cannot be overstated, the failure of axons to regenerate after spinal cord injury still remains one of the greatest challenges facing both medicine and neuroscience. Unlike the myelinated axons of the peripheral nervous system, myelinated axons of the central nervous system do not regenerate after being severed. An important development, however, has been the identification of inhibitory proteins in the myelin sheaths that surround CNS axons. Certain bioactive molecules appear to inhibit neurite outgrowth, leading to failure of CNS neuron regeneration. Myelin contains a number of proteins that have been shown to inhibit neurite process outgrowth. NogoA, a member of the reticulon family, was the first protein identified as a neurite outgrowth inhibitor. It is expressed by oligodendrocytes and some neurons, and can be found both intracellularly and on the cell surface (particularly on the myelin sheaths of axons). Other proteins that can contribute to inhibition of axon regeneration include myelin-associated glycoprotein (MAG), oligodendrocyte-myelin glycoprotein (OMgp) and the proteoglycan versican.

Thus, it appears that the CNS environment limits axonal regeneration after injury. Indeed, CNS myelin has been identified as a major factor contributing to regenerative failure. Evidence exists that shows that CNS proteins present in the myelin sheath inhibit axonal growth and regeneration.

Various strategies have been proposed for overcoming the inhibition of axonal regeneration. One strategy that has been effective has been to elevate the levels of intracellular cAMP. This can be accomplished in several ways, such as: a peripheral conditioning lesion, administration of cAMP analogues, priming with neurotrophins or treatment with the phosphodiesterase inhibitor rolipram (PDE4 inhibitor). The effects of cAMP may be transcription dependent, and cAMP-mediated activation of CREB may lead to upregulation and expression of genes such as arginase I and interleukin-6. The products of these genes are believed to promote axonal regeneration, which raises the possibility that other cAMP-regulated genes could yield additional agents that would be beneficial in the treatment of spinal cord injury. However, with regard to increasing the expression of IL-6, one significant disadvantage to this mechanism of action may be that IL-6 is a potentially harmful pro-inflammatory cytokine, meaning, it is possible that high levels of IL-6 could actually exacerbate the inflammation that occurs after spinal cord injury which could then lead to increase in cell death. Indeed, a factor supporting this concern is that IL-6 transgenic mice have been observed to have extensive astrogliosis, neurodegeneration, and breakdown of the blood brain barrier.

SUMMARY OF THE INVENTION

The invention provides for a compound of Formula V:

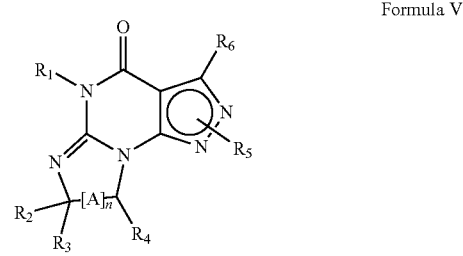

Formula V wherein
(i) $R_1$ is $C_{1-4}$ alkyl (e.g., methyl);
(ii) $R_4$ is H and $R_2$ and $R_3$ are, independently, H or $C_{1-4}$ alkyl
(e.g., $R_2$ and $R_3$ are both methyl, or $R_2$ is H and $R_3$ is isopropyl);
(iii) $R_5$ is attached to one of the nitrogens on the pyrazolo portion of Formula V and is a moiety of Formula A

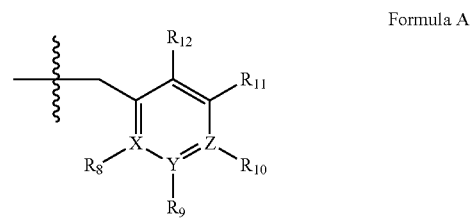

Formula A wherein X, Y and Z are C, and $R_8$, $R_9$, $R_{11}$ and $R_{12}$ are H, and $R_{10}$ is halogen (e.g. chloro), or heteroaryl optionally substituted with halogen, alkyl, haloalkyl, hydroxy or carboxy (e.g., pyridyl or 2-halopyridyl, (for example, pyrid-2-yl, 5-fluoropyrid-2-yl or 6-fluoropyrid-2-yl)); and
(iv) $R_6$ is H, $C_{1-4}$alkyl (e.g. methyl, ethyl or propyl), arylamino optionally substituted with $C_{1-4}$alkyl or halogen (e.g., phenylamino or 4-fluorophenylamino), or thio$C_{1-4}$alkyl (e.g., thioethyl); and
(v) n=0;
in free, salt or prodrug form, including its enantiomers, diastereoisomers and racemates.

In a further aspect, the invention contemplates that the PDE1 inhibitors (e.g., Formula V) are compounds of Formula V according to any of the following formulae:
1.1 The compound of Formula V, wherein $R_1$ is methyl;
1.2 The compound of Formula V or 1.1, wherein $R_2$ and $R_3$ are $C_{1-4}$ alkyl;
1.3 The compound of Formula V or any of 1.1-1.2, wherein $R_2$ and $R_3$ are both methyl;
1.4 The compound of Formula V or any of 1.1-1.3, wherein $R_{10}$ is heteroaryl optionally substituted with halogen;
1.5 The compound of Formula V or any of 1.1-1.4, wherein $R_{10}$ is pyrid-2-yl;
1.6 The compound of Formula V or any of 1.1-1.4, wherein $R_{10}$ is 5-fluoro-pyrid-2-yl;
1.7 The compound of Formula V or any of 1.1-1.4, wherein $R_{10}$ is 6-fluoro-pyrid-2-yl;

1.8 The compound of Formula V or any of 1.1-1.7, wherein $R_6$ is $C_{1-4}$-alkyl;
1.9 The compound of Formula V or any of 1.1-1.8, wherein $R_6$ is ethyl;
1.10 The compound of Formula V or any of 1.1-1.8, wherein $R_6$ is propyl;
1.11 The compound of Formula V or any of 1.1-1.7, wherein $R_6$ is arylamino optionally substituted with $C_{1-4}$alkyl or halogen;
1.12 The compound of Formula V or any of 1.1-1.7, wherein $R_6$ is 4-fluorophenylamino;
1.13 Any of the preceding formulae wherein the compound is selected from the group consisting

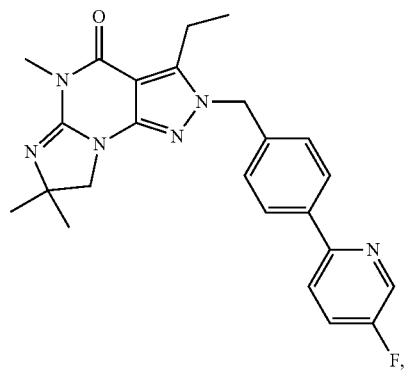

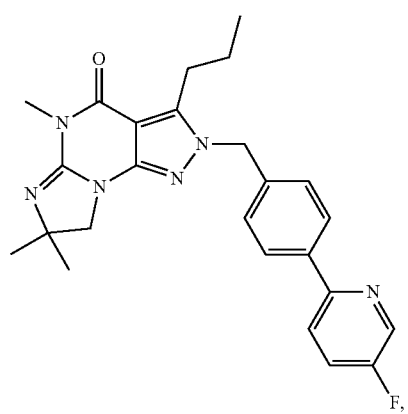

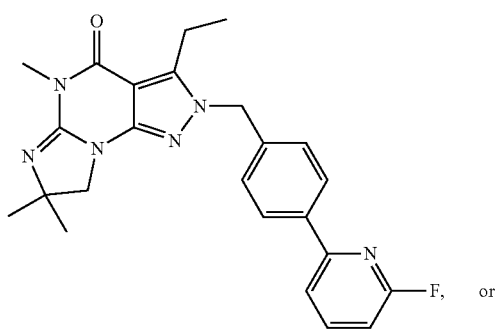

-continued

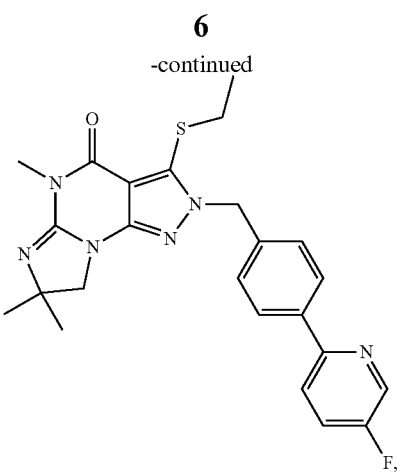

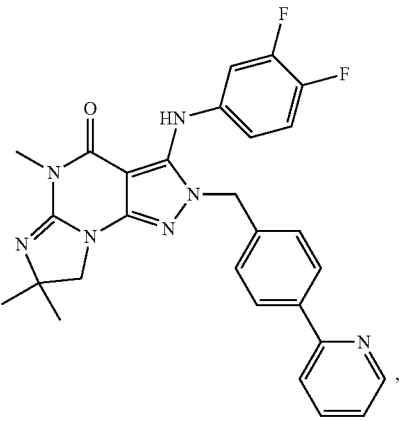

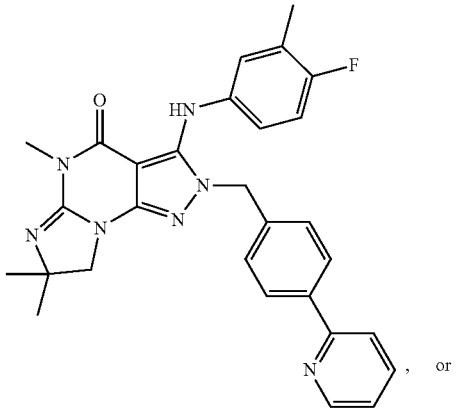

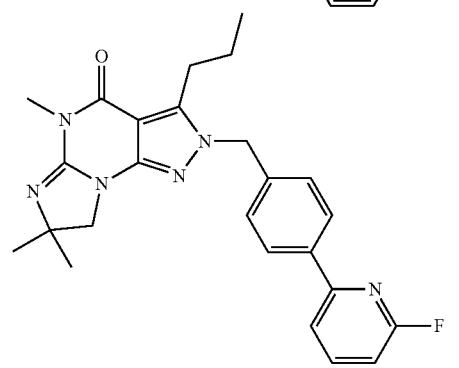

in free, salt or prodrug form, including its enantiomers, diastereoisomers and racemates.

1.14 Any of the preceding formulae wherein the compound is selected from a group consisting of:

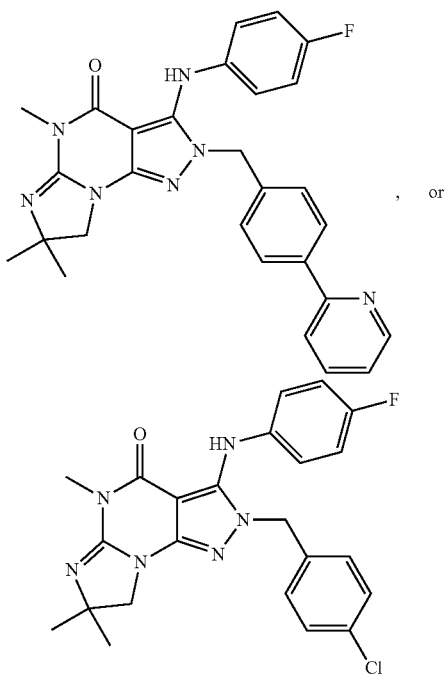

in free, salt or prodrug form, including its enantiomers, diastereoisomers and racemates.

In one aspect, selective PDE1 inhibitors of the any of the preceding formulae (e.g., Formula V or 1.1-1.14) are compounds that inhibit phosphodiesterase-mediated (e.g., PDE1-mediated, especially PDE1A or PDE1C-mediated) hydrolysis of cGMP, e.g., the preferred compounds have an IC50 of less than 1 M, preferably less than 500 nM, and more preferably less than 50 nM, in an immobilized-metal affinity particle reagent PDE assay, in free or salt form.

It is one advantage of the present invention that a PDE1 inhibitor (e.g., a compound of any of Formula V or 1.1-1.14) may act as a neuroprotective agent and/or neuroregenerative agent. In the event of a CNS injury (e.g., spinal cord injury), disease, or disorder, the compounds and methods disclosed herein may be employed to aid or enhance neurite outgrowth and axonal regeneration even in the presence of inhibitors of axonal regeneration.

Without being bound by any particular theory, it is believed that at least one advantage of the present invention is that the administration of a PDE1 inhibitor (e.g., any compound of Formula V or 1.1-1.14) may act to increase levels of intracellular cAMP and initiate the transcription of genes that are necessary for overcoming the inhibition of axonal regeneration and promoting neurite outgrowth and/or axonal regeneration in the case of a CNS disease, disorder, or injury. For instance, increased intracellular cAMP, such as would result from PDE1 inhibition, would lead to increased activity of cAMP-dependent proteins, such as protein kinase C (PKC).

Furthermore, it is believed that the administration of a PDE1 inhibitor (e.g., a compound of any of Formula V or 1.1-1.14) may elevate the intracellular levels of both cAMP and cGMP. Without being bound by theory, this rise in both cAMP and cGMP may serve to counterbalance the potentially detrimental effects that may be associated with chronically elevated levels of intracellular calcium. It has been observed that elevated levels of intracellular calcium may be associated with the development of various degenerative diseases. For instance, one possible explanation is that elevated levels of intracellular calcium (e.g., chronically elevated levels of intracellular calcium) leads to the activation of PDE1, which then stimulates cAMP hydrolysis. The decreased concentration of cAMP would then deactivate cAMP-dependent proteins such as protein kinase C (PKC).

However, without being bound by any theory, it is believed that another potential benefit of the administration of a PDE1 inhibitor (e.g., a compound of any of Formula V or 1.1-1.14) is an increase in intracellular cGMP. This increase in intracellular cGMP may lead to an increase in the activity of PKG, preventing a further rise in intracellular calcium levels. Thus, without being bound by any theory, the administration of a PDE1 inhibitor (e.g., a compound of any of Formula V or 1.1-1.14) could have the dual benefit of, for example, playing a beneficial role in axonal regeneration (and/or neuroprotection) while simultaneously decreasing the deleterious effects that may be associated with elevated intracellular calcium levels.

In one embodiment the invention comprises compositions and methods to treat or prevent a CNS disease, disorder, or injury (e.g., spinal cord injury, e.g., spinal muscular atrophy, e.g., motor neuron injury), wherein the method comprises administration of an effective amount of a PDE1 inhibitor (e.g., a compound of any of Formula V or 1.1-1.14) to modulate intracellular levels of cAMP and/or cGMP. In one embodiment, this increase in intracellular cAMP is neuroprotective and/or aids in the increase or stimulation of neurogenesis (e.g., the PDE1 inhibitor increases neurite outgrowth and/or axonal regeneration).

In still a further embodiment, the invention comprises compositions and methods to treat or prevent injuries to the peripheral nervous system (PNS) wherein the method comprises administration of a PDE1 inhibitor to increase intracellular levels of cAMP and/or cGMP which, either directly or indirectly, increases nerve regeneration and/or is protective against further nerve damage.

In one embodiment the invention comprises compositions and methods to prevent a CNS disease or disorder in a subject that is at risk for developing said disease or disorder, wherein the method comprises:
1.) Obtaining a CNS sample from the subject;
2.) Measuring the levels of intracellular calcium from the sample;
3.) Comparing the levels of intracellular calcium in the biological sample to a reference standard;
4.) Determining whether a patient is at risk for developing a CNS disease or disorder based upon the level of intracellular calcium compared to the reference standard;
5.) Administering a PDE1 inhibitor (e.g., a compound of any of Formula V or 1.1-1.14) to a subject based upon the subject's levels of intracellular calcium (e.g., administration of a PDE1 inhibitor to a subject because they have elevated intracellular calcium levels compared to the reference standard).

If not otherwise specified or clear from context, the following terms herein have the following meanings:
  (a) "Alkyl" as used herein is a saturated or unsaturated hydrocarbon moiety, preferably saturated, preferably having one to six carbon atoms, which may be linear or branched, and may be optionally mono-, di- or tri-substituted, e.g., with halogen (e.g., chloro or fluoro), hydroxy, or carboxy.
  (b) "Cycloalkyl" as used herein is a saturated or unsaturated nonaromatic hydrocarbon moiety, preferably saturated, preferably comprising three to nine carbon atoms, at least some of which form a nonaromatic mono- or bicyclic, or bridged cyclic structure, and which may be optionally substituted, e.g., with halogen (e.g., chloro or fluoro), hydroxy, or carboxy. Where the cycloalkyl optionally contains one or more atoms selected from N and O and/or S, said cycloalkyl may also be a heterocycloalkyl.

(c) "Heterocycloalkyl" is, unless otherwise indicated, a saturated or unsaturated nonaromatic hydrocarbon moiety, preferably saturated, preferably comprising three to nine carbon atoms, at least some of which form a nonaromatic mono- or bicyclic, or bridged cyclic structure, wherein at least one carbon atom is replaced with N, O or S, which heterocycloalkyl may be optionally substituted, e.g., with halogen (e.g., chloro or fluoro), hydroxy, or carboxy.

(d) "Aryl" as used herein is a mono or bicyclic aromatic hydrocarbon, preferably phenyl, optionally substituted, e.g., with alkyl (e.g., methyl), halogen (e.g., chloro or fluoro), haloalkyl (e.g., trifluoromethyl), hydroxy, carboxy, or an additional aryl or heteroaryl (e.g., biphenyl or pyridylphenyl).

(e) "Heteroaryl" as used herein is an aromatic moiety wherein one or more of the atoms making up the aromatic ring is sulfur or nitrogen rather than carbon, e.g., pyridyl or thiadiazolyl, which may be optionally substituted, e.g., with alkyl, halogen, haloalkyl, hydroxy or carboxy.

(f) It is intended that wherein the substituents end in "ene", for example, alkylene, phenylene or arylalkylene, said substitutents are intended to bridge or be connected to two other substituents. Therefore, methylene is intended to be —$CH_2$— and phenylene intended to be —$C_6H_4$— and arylalkylene is intended to be, for example, —$C_6H_4$—$CH_2$— or —$CH_2$—$C_6H_4$—.

In this specification, unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included Compounds of the Invention, encompassing any of the compounds disclosed herein, may exist in free or salt form, e.g., as acid addition salts. In this specification unless otherwise indicated, language such as "Compounds of the Invention" is to be understood as embracing the compounds in any form, for example free or acid addition salt form, or where the compounds contain acidic substituents, in base addition salt form. The Compounds of the Invention are intended for use as pharmaceuticals, therefore pharmaceutically acceptable salts are preferred. Salts which are unsuitable for pharmaceutical uses may be useful, for example, for the isolation or purification of free Compounds of the Invention or their pharmaceutically acceptable salts, are therefore also included.

Compounds of the Invention may in some cases also exist in prodrug form. A prodrug form is a compound which converts in the body to a Compound of the Invention. For example when the Compounds of the Invention contain hydroxy or carboxy substituents, these substituents may form physiologically hydrolysable and acceptable esters. As used herein, "physiologically hydrolysable and acceptable ester" means esters of Compounds of the Invention which are hydrolysable under physiological conditions to yield acids (in the case of Compounds of the Invention which have hydroxy substituents) or alcohols (in the case of Compounds of the Invention which have carboxy substituents) which are themselves physiologically tolerable at doses to be administered. Therefore, wherein the Compound of the Invention contains a hydroxy group, for example, Compound-OH, the acyl ester prodrug of such compound, i.e., Compound-O—C(O)—$C_{1-4}$alkyl, can hydrolyze in the body to form physiologically hydrolysable alcohol (Compound-OH) on the one hand and carboxylic acid on the other (e.g., HOC(O)—$C_{1-4}$alkyl). Alternatively, wherein the Compound of the Invention contains a carboxylic acid, for example, Compound-C(O)OH, the acid ester prodrug of such compound, Compound-C(O)O—$C_{1-4}$alkyl can hydrolyze to form Compound-C(O)OH and alcohol HO—$C_{1-4}$alkyl. As will be appreciated the term thus embraces conventional pharmaceutical prodrug forms.

In another embodiment, the invention further provides a pharmaceutical composition comprising a Compound of the Invention, in free or pharmaceutically acceptable salt form, in admixture with a pharmaceutically acceptable carrier.

Methods of Making Compounds of the Invention

The compounds of the Invention and their pharmaceutically acceptable salts may be made using the methods as described and exemplified herein and by methods similar thereto and by methods known in the chemical art. Such methods include, but are not limited to, those described below. If not commercially available, starting materials for these processes may be made by procedures, which are selected from the chemical art using techniques which are similar or analogous to the synthesis of known compounds.

Various starting materials and/or Compounds of the Invention may be prepared using methods described in US 2008-0188492 A1, US 2010-0173878 A1, US 2010-0273754 A1, US 2010-0273753 A1, WO 2010/065153, WO 2010/065151, WO 2010/065151, WO 2010/065149, WO 2010/065147, WO 2010/065152, WO 2011/153129, WO 2011/133224, WO 2011/153135, WO 2011/153136, WO 2011/153138, US 2014/0194396, PCT/US14/30412, and each reference is herein incorporated by reference in its entirety.

The Compounds of the Invention include their enantiomers, diastereoisomers and racemates, as well as their polymorphs, hydrates, solvates and complexes. Some individual compounds within the scope of this invention may contain double bonds. Representations of double bonds in this invention are meant to include both the E and the Z isomer of the double bond. In addition, some compounds within the scope of this invention may contain one or more asymmetric centers. This invention includes the use of any of the optically pure stereoisomers as well as any combination of stereoisomers.

It is also intended that the Compounds of the Invention encompass their stable and unstable isotopes. That is, the Compounds of the Invention embrace the replacement or enrichment of any atom, or more than one atom, of the structure by any stable or unstable isotopic variant of that atom. Isotopes are atoms of the same element that contain varying numbers of neutrons. An isotopic variant is any isotope of any element other than its naturally most abundant isotope. An isotopic variant will contain one or more additional, or one or more fewer, neutrons compared to the most naturally abundant nuclide of the same element. Isotopes may either be stable (non-radioactive) or unstable (radioactive). For example, the most naturally abundant nuclide of carbon is $^{12}C$, and one known stable isotope of carbon is $^{13}C$. Isotopes of an element generally share the same characteristic electronic and chemical properties. It is expected that the activity of compounds comprising such isotopes would be retained, and such compound would also have utility for measuring pharmacokinetics of the non-isotopic analogs. For example, the hydrogen atom at one or more atomic positions of the Compounds of the Invention may be replaced with (or enriched in) deuterium. Examples of known stable isotopes include, but are not limited to, deuterium ($^{2}H$), $^{13}C$, $^{15}N$, and $^{18}O$. Examples of known unstable isotopes include $^{3}H$, $^{123}I$, $^{131}I$, $^{125}I$, $^{11}C$, $^{18}F$. Unstable isotopes may be useful for radio-imaging and/or pharmacokinetic studies of the compounds of the invention. One or more atomic positions in a Compound of the Invention may be replaced with or enriched in any known isotopic variant. Natural sources of chemicals and reagents are not generally isotopically pure, so that Compounds of the Invention made by traditional chemical methods will generally have some normal, natural variation in isotopic abundance. For example, the natural abundance of the element carbon consists approximately of 98.93% $^{12}C$ and 1.07% $^{13}C$. Therefore, Compounds of the Invention made by traditional chemical means will typically consist of about 98.93% $^{12}C$ and 1.07% $^{13}C$ at each carbon atom of the structure. Enrichment refers to the presence of more than the natural abundance of a minor isotope in a chemical structure. Thus, for example, a Compound of the Invention may be enriched for the presence of $^{13}C$ at one or more carbon atom positions. As used herein, "replacement" refers to enrichment of an isotopic variant of greater than about 95%.

Melting points are uncorrected and "dec" indicates decomposition. Temperatures are given in degrees Celsius (° C.); unless otherwise stated, operations are carried out at room or ambient temperature, that is, at a temperature in the range of 18-25° C. Chromatography means flash chromatography on silica gel; thin layer chromatography (TLC) is carried out on silica gel plates. NMR data is presented using delta values of the major diagnostic protons, given in parts per million (ppm) relative to tetramethylsilane (TMS) as an internal standard. Conventional abbreviations for signal shape are used. Coupling constants (J) are given in Hz. For mass spectra (MS), the lowest mass major ion is reported for molecules where isotope splitting results in multiple mass spectral peaks Solvent mixture compositions are given as volume percentages or volume ratios. In cases where the NMR spectra are complex, only diagnostic signals are reported.

Terms and abbreviations:
BOC=tert-butoxycarbonyl
BOP=Benzotriazole-1-yl-oxy-tris(dimethylamino)phosphonium hexafluorophosphate
BuLi=n-butyllithium
Bu$^t$OH=tert-butyl alcohol,
CAN=ammonium cerium (IV) nitrate,
DBU=1,8-diazabicyclo[5.4.0]undec-7-ene,
DIPEA=diisopropylethylamine,
DMF=N,N-dimethylforamide,
DMSO=dimethyl sulfoxide,
Et$_2$O=diethyl ether,
EtOAc=ethyl acetate,
equiv.=equivalent(s),
h=hour(s),
HPLC=high performance liquid chromatography,
LDA=lithium diisopropylamide MeOH=methanol,
NBS=N-bromosuccinimide
NCS=N-chlorosuccinimide
NaHCO$_3$=sodium bicarbonate,
NH$_4$OH=ammonium hydroxide,
Pd$_2$(dba)$_3$=tris[dibenzylideneacetone]dipalladium(0)
PMB=p-methoxybenzyl,
POCl$_3$=phosphorous oxychloride,
SOCl$_2$=thionyl chloride,
TFA=trifluoroacetic acid,
TFMSA=trifluoromethanesulfonic acid
THF=tetrahedrofuran.

The synthetic methods useful in this invention are illustrated below. The definitions for the R groups are as set forth above for any of Formulae V or 1.1-1.14, unless otherwise indicated.

Intermediate compounds of formula IIb can be prepared by reacting a compound of formula IIa with malonic acid and acetic anhydride in acetic acid, optionally with heating (e.g., to about 90° C. for about 3 hours):

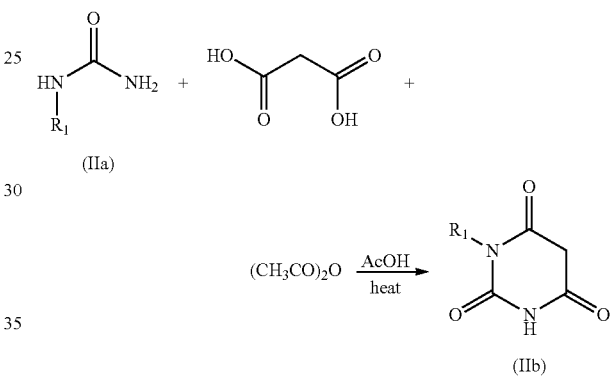

wherein R$_1$ is C$_{1-4}$ alkyl, e.g., methyl.

Intermediates of formula IIc can be prepared by reacting a compound of formula IIb with a chlorinating compound such as POCl$_3$, optionally with small amounts of water and/or heating (e.g., heating to about 80° C. for about 4 hours):

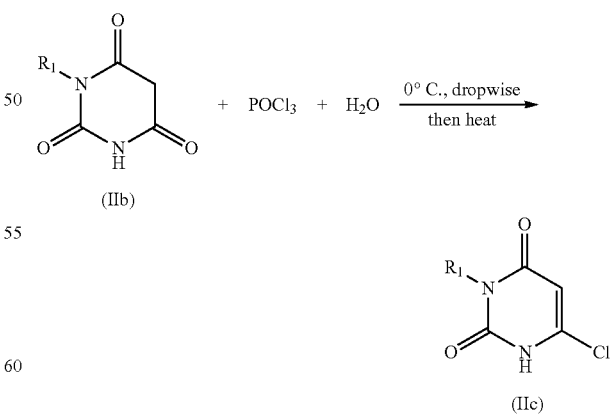

Intermediates of formula IId may be prepared by reacting compounds of formula IIc with, for example, a reagent P$^1$-L in a solvent such as DMF, with a base such as potassium carbonate, sodium bicarbonate, cesium carbonate, sodium hydroxide, triethylamine, diisopropylethylamine or the like, at room temperature or with heating:

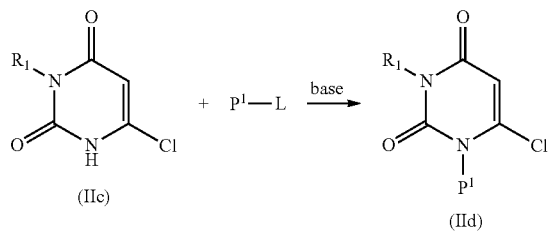

wherein $P^1$ is a protective group (e.g., PMB or BOC); and L is a leaving group such as a halogen, mesylate, or tosylate. Preferably, $P^1$ is PMB and the base is potassium carbonate.

Intermediates of formula IIe may be prepared by reacting compounds of formula IId with hydrazine or hydrazine hydrate in a solvent such as methanol, preferably with heating (e.g. reflux for about 4 hours):

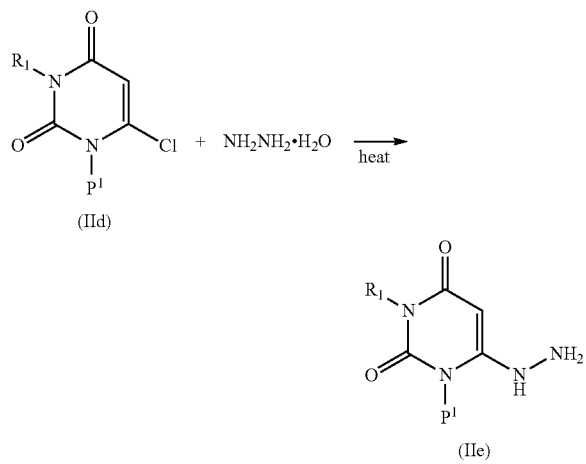

Intermediates of formula IVa may be prepared by reacting compound of formula IIe with POCl$_3$ and DMF:

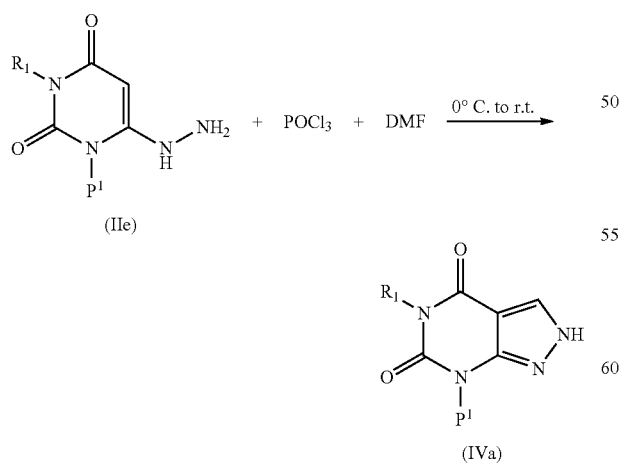

Intermediates of formula IVb may be prepared by reacting a compound of formula IVa with a reagent of formula $F^1$—X in a solvent such as DMF with a base such as potassium carbonate at room temperature:

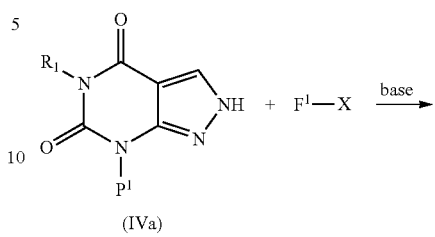

wherein $F^1$ is a protecting group (e.g., a substituted benzyl group, such as 4-bromobenzyl), and X is a halogen (e.g., Br).

Intermediates of formula IVc may be prepared from compounds of formula IVb by removing the protective group $P^1$ using an appropriate method. For example, if $P^1$ is a PMB group, then it can be removed with TFA/TFMSA at ambient or elevated temperature, whereas if P1 is BOC, then it can be removed using an acid such as TFA or aqueous hydrochloric acid:

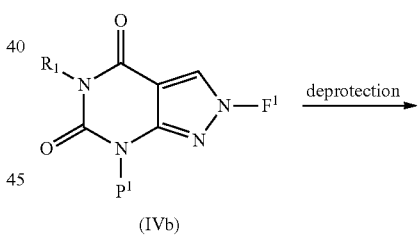

Intermediates of formula IVd can be prepared by reacting a compound of formula IVc with a chlorinating compound such as POCl$_3$, optionally with heating (e.g., reflux for 2 days or more, or microwave irradiation at 150-200° C. for 5-10 minutes in a sealed vial):

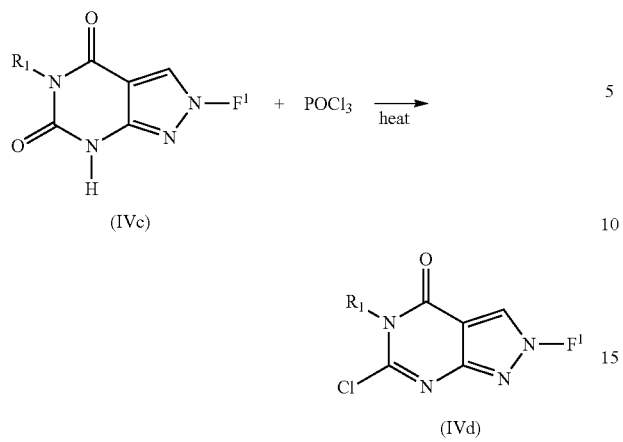

(IVc) + POCl₃ →(heat)

(IVd)

Intermediates of formula IVe can be prepared by reacting a compound of formula IVd with an amino alcohol under basic condition in a solvent such as DMF, optionally with heating:

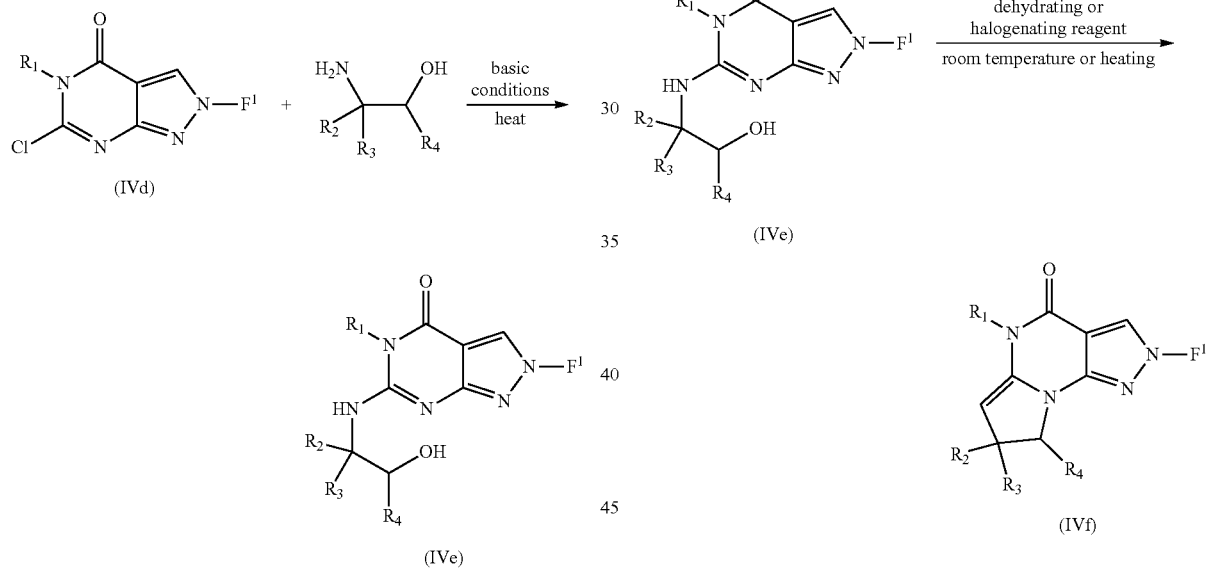

(IVe)

wherein $R_1$, $R_2$, $R_3$, and $R_4$ are as defined previously for any of Formulae V or 1.1-1.14.

Alternatively, intermediates IVe can be prepared directly from compounds of formula IVc by reacting with an amino alcohol and a coupling reagent such as BOP in the presence of a base such as DBU:

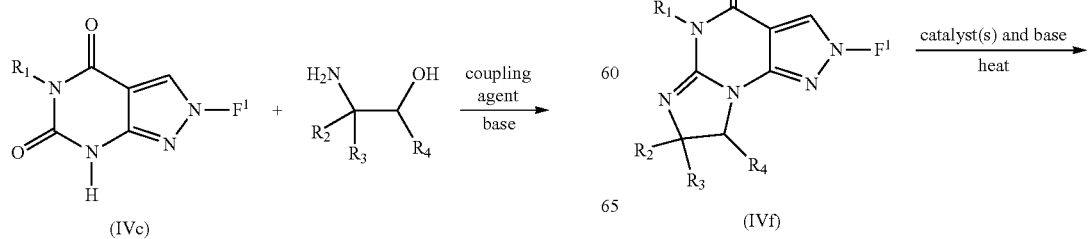

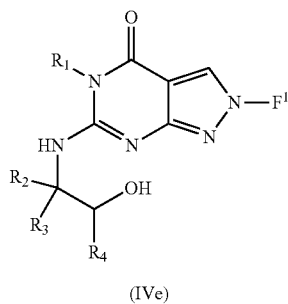

(IVe)

wherein $R_1$, $R_2$, $R_3$, and $R_4$ are as defined previously for any of Formulae V or 1.1-1.14.

Intermediates of formula IVf may be prepared by reacting a compound of formula IVe with a dehydrating/halogenating agent such as SOCl₂ in a solvent such as dichloromethane at room temperature or with heating at 35° C.:

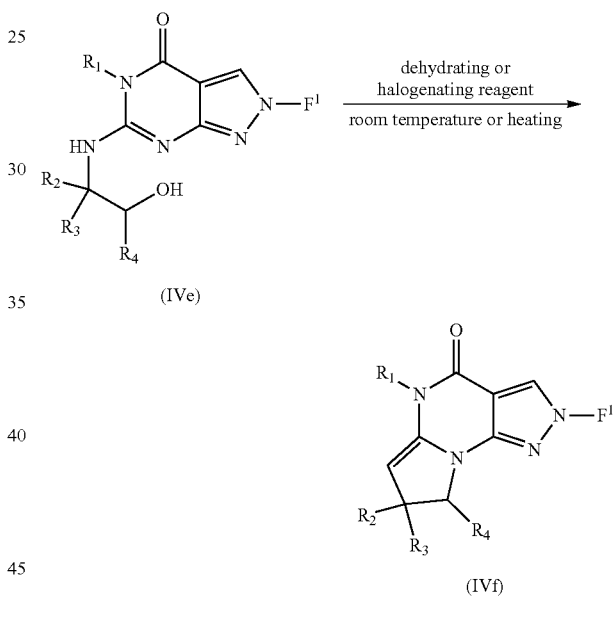

(IVf)

Intermediates of formula IVg may be prepared by reacting a compound of formula IVf with, catalysts such as a copper salt and 2,2,6,6-tetramethylheptane-3,5-dione and a base such as cesium carbonate in a solvent such as NMP with heating:

(IVf)

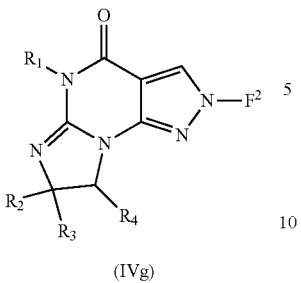

(IVg)

wherein, F² is a diaryl ether.

Intermediates of formula IVh may be prepared by reacting a compound of formula IVg with an acidic system, such as TFA and TFMSA in a solvent such as dichloromethane, at room temperature:

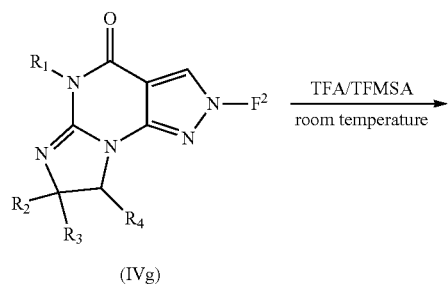

(IVh)

Intermediates of formula IVi may be prepared by reacting a compound of formula IVh with a reagent of formula $R_5$—$(CH_2)_n$-L in the presence of a base such as potassium carbonate, in a solvent such as DMF at room temperature:

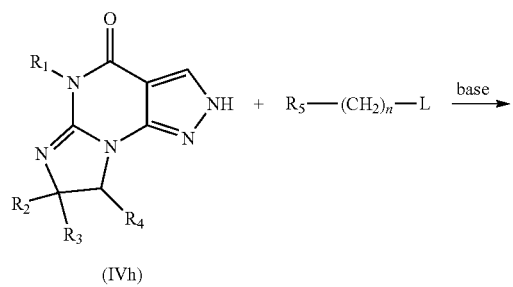

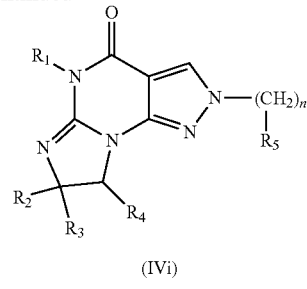

(IVi)

wherein n is 0, and $R_5$ is a moiety of Formula A, as defined previously for any of Formulae V or 1.1-1.14, and L is a leaving group such as a halogen (e.g., Br).

Intermediates of formula IVj, wherein X is halogen (e.g., Cl), may be prepared by reacting compounds of formula IVi with a halogenating agent (e.g. NCS or NBS) and a base such as LiHMDS in a solvent such as THF at low temperature:

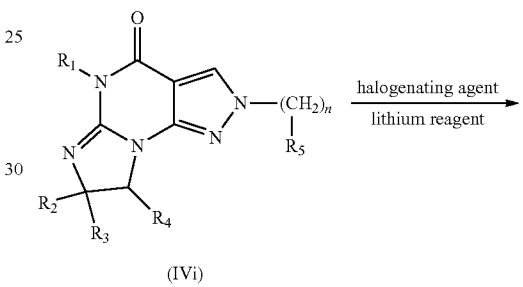

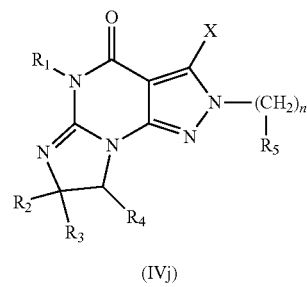

(IVj)

Compounds of the Invention, may then be prepared from compounds of Formula IVj by methods known to those skilled in the art. For example, by displacement of the halogen X with an arylamine or an alkylmercaptan.

Methods of Using Compounds of the Invention

The invention further provides Method I, wherein Method I comprises the prophylaxis and/or treatment of diseases, disorders, and injuries of the central nervous system, wherein the method comprises the administration of an effective amount of a PDE1 inhibitor (e.g., any compound of Formula V or 1.1-1.14) to modulate the level of intracellular cAMP.

For example, Method I also includes:
1.1. Method I, wherein the administration of the PDE1 inhibitor enhances the axonal growth or regeneration, and/or slows or reverses the loss of such cells in a neurodegenerative condition.
1.2. Any of preceding Method-I, et seq., wherein the CNS disease, disorder, or injury, refers to damage that directly or indirectly affects the normal functioning of the CNS.

1.3. Any of preceding Method-I, et seq., wherein the CNS disease, disorder, or injury can be a structural, physical, or mechanical impairment and may be caused by physical impact, e.g., crushing, compression, or stretching of nerve fibers.

1.4. Any of preceding Method-I, et seq., wherein the CNS disease, disorder, or injury is a spinal cord injury.

1.5. Method of 1.4, wherein the PDE1 inhibitor slows or arrests the progression of the spinal cord injury.

1.6. Any of preceding Method-I, et seq., wherein the PDE1 inhibitor slows or arrests axonal filament degradation.

1.7. Any of preceding Method-I, et seq. wherein the CNS disease, disorder, or injury relates to motor neuron trauma.

1.8. Any of preceding Method-I, et seq., wherein the disease, disorder, or injury is selected from the group consisting of: neurological traumas and injuries, surgery related trauma and/or injury, retinal injury and trauma, injury related to epilepsy, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxins, and spinal cord injury related to environmental toxins.

1.9. Any of preceding Method-I, et seq., wherein the CNS disease, disorder, or injury includes neuron or nerve fibers destroyed by or degraded by an illness (e.g., Parkinson's Disease), a chemical imbalance, or a physiological malfunction such anoxia (e.g., stroke), aneurysm, or reperfusion injury.

1.10. Any of preceding Method-I, et seq., wherein the CNS disease, disorder, or injury is a neurodegenerative disorder.

1.11. Method of 1.10, wherein the neurodegenerative disease, disorder, or injury is selected from the group consisting of: Alzheimer's disease, Multiple Sclerosis, Spinal Muscular Atrophy, Glaucoma, Frontotemporal dementia, Dementia with Lewy bodies, Corticobasal degeneration, Progressive supranuclear palsy, Prion disorders, Huntington's disease, Multiple system atrophy, Parkinson's disease, Amyotrophic lateral sclerosis, Hereditary spastic paraparesis, Spinocerebellar atrophies, Friedreich's ataxia, Amyloidoses, Metabolic (diabetes) related disorders, Toxin related disorders, chronic CNS inflammation, Charcot Marie Tooth disease, diabetic neuropathy, injury due to cancer chemotherapy (e.g., by vinca alkaloids and doxorubicin), brain damage associated with stroke, ischemia associated with stroke, and neurological disorders including, but not limited to, various peripheral neuropathic and neurological disorders related to neurodegeneration including, but not limited to: trigeminal neuralgia, glossopharyngeal neuralgia, Bell's palsy, myasthenia gravis, muscular dystrophy, amyotrophic lateral sclerosis, progressive muscular atrophy, progressive bulbar inherited muscular atrophy, herniated, ruptured or prolapsed vertebral disk syndromes, cervical spondylosis, plexus disorders, thoracic outlet destruction syndromes, peripheral neuropathies such as those caused by e.g., lead, acrylamides, gamma-diketones, carbon disulfide, dapsone, ticks, porphyria, and Gullain-Barre syndrome.

1.12. Any of preceding Method-I, et seq., wherein the CNS disease, disorder, or injury is a CNS lesion, a seizure or injury due to seizures (e.g., epileptic seizures), radiation injury, injury due to chemotherapy and/or stroke or other ischemic injury.

1.13. Any of preceding Method-I, et seq., wherein the administration of the PDE1 inhibitor is used to replenish, replace, and/or supplement neurons and/or glial cells.

1.14. Any of preceding Method-I, et seq., wherein the PDE1 inhibitor is administered to a subject or a patient in need thereof.

1.15. Any of preceding Method-I, et seq., wherein the PDE1 inhibitor elevates the level or expression of intracellular cAMP.

1.16. Any of preceding Method-I, et seq., wherein the PDE1 inhibitor decreases the level or expression of intracellular cAMP.

1.17. Any of preceding Method-I, et seq., wherein the PDE1 modulates activity of PKA or PKG.

1.18. Any of preceding Method-I, et seq., wherein the PDE1 inhibitor increases the activity of PKA or PKG.

1.19. Any of preceding Method-I, et seq., wherein the administration of the PDE1 inhibitor increases the level of both cAMP and cGMP.

1.20. Any of preceding Method-I, et seq., wherein the administration of the PDE1 inhibitor elevates the level of intracellular cAMP, and wherein this increased level intracellular cAMP has neuroprotective and/or neuroregenerative effects.

1.21. Any of preceding Method-I, et seq., comprising administration of an effective amount of the PDE1 inhibitor to a patient that suffers from a disease or disorder related to elevated (e.g., chronically elevated) intracellular calcium levels, and wherein the PDE1 inhibitor prevents a further rise in said calcium levels.

1.22. Any of preceding Method-I, et seq., wherein the PDE1 inhibitor is administered either alone or in combination with another active agent.

1.23. Any of preceding Method-I, et seq., wherein the disease, disorder, or injury is related to motor neurons, and wherein the motor neuron disease, disorder, or injury is Multiple Sclerosis.

1.24. Any of preceding Method-II, et seq., wherein the PDE1 inhibitor is administered in combination with another active agent in order to treat Multiple Sclerosis.

1.25. The method of 2.11, wherein the active agent is selected from the group consisting of: Interferon, Glatiramer acetate, Natalizumab, Gilenya® (fingolimod), Fampyra®, immunosuppressents, and corticoids.

In another embodiment the invention provides for Method II, wherein Method II comprises compositions and methods of treatment or prophylaxis of a peripheral nervous system (PNS) disease, disorder, or injury, wherein the method comprises administration of an effective amount of a PDE1 inhibitor (e.g., any compound of Formula V or 1.1-1.14) to increase intracellular levels of cAMP.

For example, Method II also includes:
2.1. Method II, wherein the PNS disease, disorder, or injury, refers to damage that directly or indirectly affects the normal functioning of the CNS.

2.2. Any of preceding Method-II, et seq., wherein the PDE1 inhibitor is administered to a subject or a patient in need thereof.

2.3. Any of preceding Method-II, et seq., wherein the PDE1 inhibitor elevates the level or expression of intracellular cAMP.

2.4. Any of preceding Method-II, et seq., wherein the PDE1 inhibitor (e.g., directly or indirectly) modulates activity of PKA and/or PKG.
2.5. Any of preceding Method-II, et seq., wherein the PDE1 inhibitor (e.g., directly or indirectly) increases the activity of PKA and/or PKG.
2.6. Any of preceding Method-II, et seq., wherein the administration of the PDE1 inhibitor increases the level of cAMP and/or cGMP.
2.7. Any of preceding Method-II, et seq., wherein the administration of the PDE1 inhibitor elevates the level of intracellular cAMP, and wherein this increased level intracellular cAMP levels protects nerve fibers, regenerates nerve fibers, or promotes nerve fiber growth (e.g., axonal regeneration).
2.8. Any of preceding Method-II, et seq., comprising administration of an effective amount of the PDE1 inhibitor to a patient that suffers from a disease or disorder related to elevated (e.g., chronically elevated) intracellular calcium levels.
2.9. Any of preceding Method-II, et seq., wherein the PDE1 inhibitor is administered either alone or in combination with another active agent.
2.10. The method of 2.9, wherein the active agent is selected from the IGF (e.g., IGF-1) or a steroid.
2.11. Any of preceding Method-II, et seq. wherein the PNS disease, disorder, or injury is selected from the group consisting of: neuropathy (e.g., peripheral neuropathy, autonomic neuropathy, and mononeuropathy), sciatica, carpal tunnel syndrome, polyneuropathy, diabetic neuropathy, postherpetic neuralgia, and thoracic outlet syndrome.

In another embodiment the invention provides for Method III, wherein Method III comprises compositions and methods to prevent a CNS disease or disorder in a subject that is at risk for developing said disease or disorder, wherein the method comprises:

1.) Obtaining a sample from the subject;
2.) Measuring the levels of intracellular calcium from the sample;
3.) Comparing the levels of intracellular calcium in the biological sample to a reference standard;
4.) Determining whether a patient is at risk for developing a CNS disease or disorder based upon the level of intracellular calcium compared to the reference standard;
5.) Administering a PDE1 inhibitor (e.g., a compound of any of Formula V or 1.1-1.14) to a subject based upon the subject's levels of intracellular calcium (e.g., administration of a PDE1 inhibitor to a subject because they have elevated intracellular calcium levels compared to the reference standard).

For example, Method III also includes:
3.1. Method III, wherein the sample is a biological sample.
3.2. Any of preceding Method-III, et seq., wherein the patient's intracellular calcium levels are measured using a chemical fluorescent probe.
3.3. Any of preceding Method-III, et seq., wherein the patient's intracellular calcium levels are elevated compared to a control (e.g., reference standard).
3.4. Any of preceding Method-III, et seq., wherein a PDE1 inhibitor is administered to a patient that is shown to have elevated intracellular calcium levels compared to a control (e.g., reference standard).
3.5. Any of preceding Method-III, et seq., wherein the administration of a PDE1 inhibitor slows or prevents the development of a CNS and/or PNS disease or disorder, wherein the CNS disease or disorder is one that correlates to elevated (e.g., chronically elevated) levels of intracellular calcium.
3.6. Any of preceding Method-III, et seq., wherein the administration of a PDE1 inhibitor decreases the likelihood that an individual will develop a CNS and/or PNS disease or disorder, wherein the CNS and/or PNS disease or disorder is one that correlates with elevated (e.g., chronically elevated) levels of intracellular calcium (e.g., any of the diseases, disorders or injuries listed in Method I, et seq., and Method II, et seq.).
3.7. Any of preceding Method-III, et seq., wherein the method optionally comprises measuring the patient's intracellular levels of cAMP or cGMP.
3.8. Any of preceding Method-III, et seq., wherein the PDE1 inhibitor is administered either alone or in combination with another active agent.
3.9. Any of preceding Method-III, et seq., wherein the PDE1 inhibitor is administered because a patient has low levels of cAMP and/or cGMP compared to a control subject.

The Compounds of the Invention are useful in the treatment of diseases characterized by disruption of or damage to cAMP and cGMP mediated pathways, e.g., as a result of increased expression of PDE1 or decreased expression of cAMP and cGMP due to inhibition or reduced levels of inducers of cyclic nucleotide synthesis, such as dopamine and nitric oxide (NO). By preventing the degradation of cAMP and cGMP by PDE1, thereby increasing intracellular levels of cAMP and cGMP, the Compounds of the Invention potentiate the activity of cyclic nucleotide synthesis inducers.

In another embodiment, the invention also provides methods of treatment, wherein the method comprises administering an effective amount of a PDE1 inhibitor (e.g., any compound of Formula V or 1.1-1.14) to treat any one or more of the following conditions:

(i) Neurodegenerative diseases, including Parkinson's disease, restless leg, tremors, dyskinesias, Huntington's disease, Alzheimer's disease, and drug-induced movement disorders;
(ii) Mental disorders, including depression, attention deficit disorder, attention deficit hyperactivity disorder, bipolar illness, anxiety, sleep disorders, e.g., narcolepsy, cognitive impairment, e.g., cognitive impairment of schizophrenia, dementia, Tourette's syndrome, autism, fragile X syndrome, psychostimulant withdrawal, and drug addiction;
(iii) Circulatory and cardiovascular disorders, including cerebrovascular disease, stroke, congestive heart disease, hypertension, pulmonary hypertension, e.g., pulmonary arterial hypertension, and sexual dysfunction, including cardiovascular diseases and related disorders as described in International Application No. PCT/US2014/16741, the contents of which are incorporated herein by reference;
(iv) Respiratory and inflammatory disorders, including asthma, chronic obstructive pulmonary disease, and allergic rhinitis, as well as autoimmune and inflammatory diseases;
(v) Diseases that may be alleviated by the enhancement of progesterone-signaling such as female sexual dysfunction;
(vi) A disease or disorder such as psychosis, glaucoma, or elevated intraocular pressure;
(vii) Traumatic brain injury;

(viii) Any disease or condition characterized by low levels of cAMP and/or cGMP (or inhibition of cAMP and/or cGMP signaling pathways) in cells expressing PDE1; and/or (ix) Any disease or condition characterized by reduced dopamine D1 receptor signaling activity, comprising administering an effective amount of a Compound of the Invention, e.g., a compound according to any of (e.g., any compound of Formula V or 1.1-1.14), in free or pharmaceutically acceptable salt or prodrug form, to a human or animal patient in need thereof.

In one aspect, the invention provides methods of treatment or prophylaxis for narcolepsy. In this embodiment, PDE1 Inhibitors (e.g., any compound of Formula V or 1.1-1.14) may be used as a sole therapeutic agent, but may also be used in combination or for co-administration with other active agents. Thus, the invention further comprises a method of treating narcolepsy comprising administering simultaneously, sequentially, or contemporaneously therapeutically effective amounts of (i) a PDE1 Inhibitor, e.g., a compound according to any of (e.g., any compound of Formula V or 1.1-1.14), and (ii) a compound to promote wakefulness or regulate sleep, e.g., selected from (a) central nervous system stimulants-amphetamines and amphetamine like compounds, e.g., methylphenidate, dextroamphetamine, methamphetamine, and pemoline; (b) modafinil, (c) antidepressants, e.g., tricyclics (including imipramine, desipramine, clomipramine, and protriptyline) and selective serotonin reuptake inhibitors (including fluoxetine and sertraline); and/or (d) gamma hydroxybutyrate (GHB), in free or pharmaceutically acceptable salt or prodrug form, to a human or animal patient in need thereof.

In another aspect, the invention further provides methods of treatment or prophylaxis of a condition which may be alleviated by the enhancement of the progesterone signaling comprising administering an effective amount of a Compound of the Invention, e.g., a compound according to any of Formula V or 1.1-1.14, in free or pharmaceutically acceptable salt or prodrug form, to a human or animal patient in need thereof. Diseases or conditions that may be ameliorated by enhancement of progesterone signaling include, but are not limited to, female sexual dysfunction, secondary amenorrhea (e.g., exercise amenorrhoea, anovulation, menopause, menopausal symptoms, hypothyroidism), pre-menstrual syndrome, premature labor, infertility, for example infertility due to repeated miscarriage, irregular menstrual cycles, abnormal uterine bleeding, osteoporosis, autoimmmune disease, multiple sclerosis, prostate enlargement, prostate cancer, and hypothyroidism. For example, by enhancing progesterone signaling, the PDE1 inhibitors may be used to encourage egg implantation through effects on the lining of uterus, and to help maintain pregnancy in women who are prone to miscarriage due to immune response to pregnancy or low progesterone function. The novel PDE1 inhibitors, e.g., as described herein, may also be useful to enhance the effectiveness of hormone replacement therapy, e.g., administered in combination with estrogen/estradiol/estriol and/or progesterone/progestins in postmenopausal women, and estrogen-induced endometrial hyperplasia and carcinoma. The methods of the invention are also useful for animal breeding, for example to induce sexual receptivity and/or estrus in a nonhuman female mammal to be bred.

In this aspect, PDE1 Inhibitors may be used in the foregoing methods of treatment or prophylaxis as a sole therapeutic agent, but may also be used in combination or for co-administration with other active agents, for example in conjunction with hormone replacement therapy. Thus, the invention further comprises a method of treating disorders that may be ameliorated by enhancement of progesterone signaling comprising administering simultaneously, sequentially, or contemporaneously therapeutically effective amounts of (i) a PDE1 Inhibitor, e.g., a compound according to any of Formula V or 1.1-1.14, and (ii) a hormone, e.g., selected from estrogen and estrogen analogues (e.g., estradiol, estriol, estradiol esters) and progesterone and progesterone analogues (e.g., progestins)

in free or pharmaceutically acceptable salt or prodrug form, to a human or animal patient in need thereof.

The invention also provides a method for enhancing or potentiating dopamine D1 intracellular signaling activity in a cell or tissue comprising contacting said cell or tissue with an amount of a Compound of the Invention, e.g., a compound according to any of Formula V or 1.1-1.14, in free or pharmaceutically acceptable salt or prodrug form, sufficient to inhibit PDE1 activity.

The invention also provides a method for treating a PDE1-related disorder, a dopamine D1 receptor intracellular signaling pathway disorder, or disorders that may be alleviated by the enhancement of the progesterone signaling pathway in a patient in need thereof comprising administering to the patient an effective amount of a Compound of the Invention, e.g., a compound according to any of Formula V or 1.1-1.14, in free or pharmaceutically acceptable salt or prodrug form, that inhibits PDE1, wherein PDE1 activity modulates phosphorylation of DARPP-32 and/or the GluR1 AMPA receptor.

In another aspect, the invention also provides a method for the treatment for glaucoma or elevated intraocular pressure comprising topical administration of a therapeutically effective amount of a PDE1 Inhibitor of the Invention, e.g., a compound according to any of Formula V or 1.1-1.14, in free or pharmaceutically acceptable salt form, in an ophthalmically compatible carrier to the eye of a patient in need thereof. However, treatment may alternatively include a systemic therapy. Systemic therapy includes treatment that can directly reach the bloodstream, or oral methods of administration, for example.

The invention further provides a pharmaceutical composition for topical ophthalmic use comprising a PDE1 inhibitor; for example an ophthalmic solution, suspension, cream or ointment comprising a PDE1 Inhibitor of the Invention, e.g., a compound according to any of Formula V or 1.1-1.14, in free or ophthalmologically acceptable salt form, in combination or association with an ophthalmologically acceptable diluent or carrier.

Optionally, the PDE1 inhibitor (e.g., any of Formula V or 1.1-1.14) may be administered sequentially or simultaneously with a second drug useful for treatment of glaucoma or elevated intraocular pressure. Where two active agents are administered, the therapeutically effective amount of each agent may be below the amount needed for activity as monotherapy. Accordingly, a subthreshold amount (i.e., an amount below the level necessary for efficacy as monotherapy) may be considered therapeutically effective and may also be referred alternatively as an effective amount. Indeed, an advantage of administering different agents with different mechanisms of action and different side effect profiles may be to reduce the dosage and side effects of either or both agents, as well as to enhance or potentiate their activity as monotherapy.

The invention thus provides the method of treatment of a condition selected from glaucoma and elevated intraocular pressure comprising administering to a patient in need thereof an effective amount, e.g., a subthreshold amount, of an agent known to lower intraocular pressure concomitantly, simultaneously or sequentially with an effective amount, e.g., a subthreshold amount, of a PDE1 Inhibitor of the Invention, e.g., a compound according to any of Formula V or 1.1-1.14, in free or pharmaceutically acceptable salt form, such that amount of the agent known to lower intraocular pressure and the amount of the PDE1 inhibitor in combination are effective to treat the condition.

In one aspect, one or both of the agents are administered topically to the eye. Thus the invention provides a method of reducing the side effects of treatment of glaucoma or elevated intraocular pressure by administering a reduced dose of an agent known to lower intraocular pressure concomitantly, simultaneously or sequentially with an effective amount of a PDE1 inhibitor. However, methods other than topical administration, such as systemic therapeutic administration, may also be utilized.

The optional additional agent or agents for use in combination with a PDE1 inhibitor may, for example, be selected from the existing drugs comprise typically of instillation of a prostaglandin, pilocarpine, epinephrine, or topical beta-blocker treatment, e.g. with timolol, as well as systemically administered inhibitors of carbonic anhydrase, e.g. acetazolamide. Cholinesterase inhibitors such as physostigmine and echothiopate may also be employed and have an effect similar to that of pilocarpine. Drugs currently used to treat glaucoma thus include, e.g., 1. Prostaglandin analogs such as latanoprost (Xalatan), bimatoprost (Lumigan) and travoprost (Travatan), which increase uveoscleral outflow of aqueous humor. Bimatoprost also increases trabecular outflow.
2. Topical beta-adrenergic receptor antagonists such as timolol, levobunolol (Betagan), and betaxolol, which decrease aqueous humor production by the ciliary body.
3. Alpha$_2$-adrenergic agonists such as brimonidine (Alphagan), which work by a dual mechanism, decreasing aqueous production and increasing uveo-scleral outflow.
4. Less-selective sympathomimetics like epinephrine and dipivefrin (Propine) increase outflow of aqueous humor through trabecular meshwork and possibly through uveoscleral outflow pathway, probably by a beta$_2$-agonist action.
5. Miotic agents (para-sympathomimetics) like pilocarpine work by contraction of the ciliary muscle, tightening the trabecular meshwork and allowing increased outflow of the aqueous humour.
6. Carbonic anhydrase inhibitors like dorzolamide (Trusopt), brinzolamide (Azopt), acetazolamide (Diamox) lower secretion of aqueous humor by inhibiting carbonic anhydrase in the ciliary body.
7. Physostigmine is also used to treat glaucoma and delayed gastric emptying.

For example, the invention provides pharmaceutical compositions comprising a PDE1 Inhibitor of the Invention, e.g., a compound according to any of Formula V or 1.1-1.14, in free or pharmaceutically acceptable salt form, and an agent selected from (i) the prostanoids, unoprostone, latanoprost, travoprost, or bimatoprost, (ii) an alpha adrenergic agonist such as brimonidine, apraclonidine, or dipivefrin and (iii) a muscarinic agonist, such as pilocarpine, in combination or association with a pharmaceutically acceptable diluent or carrier. For example, the invention provides ophthalmic formulations comprising a PDE-1 Inhibitor of the Invention, e.g., a compound according to any of Formula V or 1.1-1.14, together with bimatoprost, abrimonidine, brimonidine, timolol, or combinations thereof, in free or ophthamalogically acceptable salt form, in combination or association with an ophthamologically acceptable diluent or carrier. In addition to selecting a combination, however, a person of ordinary skill in the art can select an appropriate selective receptor subtype agonist or antagonist. For example, for alpha adrenergic agonist, one can select an agonist selective for an alpha 1 adrenergic receptor, or an agonist selective for an alpha$_2$ adrenergic receptor such as brimonidine, for example. For a beta-adrenergic receptor antagonist, one can select an antagonist selective for either $\beta_1$, or $\beta_2$, or $\beta_3$, depending on the appropriate therapeutic application. One can also select a muscarinic agonist selective for a particular receptor subtype such as $M_1$-$M_5$.

The PDE1 inhibitor may be administered in the form of an ophthalmic composition, which includes an ophthalmic solution, cream or ointment. The ophthalmic composition may additionally include an intraocular-pressure lowering agent.

In yet another example, the PDE1 Inhibitors disclosed may be combined with a subthreshold amount of an intraocular pressure-lowering agent which may be a bimatoprost ophthalmic solution, a brimonidine tartrate ophthalmic solution, or brimonidine tartrate/timolol maleate ophthalmic solution.

In addition to the above-mentioned methods, it has also been surprisingly discovered that PDE1 inhibitors (e.g., any of Formula V or 1.1-1.14) are useful to treat psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder. Without intending to be bound by any theory, it is believed that typical and atypical antipsychotic drugs such as clozapine primarily have their antagonistic activity at the dopamine D2 receptor. PDE1 inhibitors, however, primarily act to enhance signaling at the dopamine D1 receptor. By enhancing D1 receptor signaling, PDE1 inhibitors can increase NMDA receptor function in various brain regions, for example in nucleus accumbens neurons and in the prefrontal cortex. This enhancement of function may be seen for example in NMDA receptors containing the NR2B subunit, and may occur e.g., via activation of the Src and protein kinase A family of kinases.

Therefore, the invention provides a new method for the treatment of psychosis, e.g., schizophrenia, schizoaffective disorder, schizophreniform disorder, psychotic disorder, delusional disorder, and mania, such as in acute manic episodes and bipolar disorder, comprising administering a therapeutically effective amount of a phosphodiesterase-1 (PDE1) Inhibitor of the Invention, e.g., a compound according to any of Formula V or 1.1-1.14, in free or pharmaceutically acceptable salt form, to a patient in need thereof.

PDE 1 Inhibitors may be used in the foregoing methods of treatment prophylaxis as a sole therapeutic agent, but may also be used in combination or for co-administration with other active agents. Thus, the invention further comprises a method of treating psychosis, e.g., schizophrenia, schizoaffective disorder, schizophreniform disorder, psychotic disorder, delusional disorder, or mania, comprising administering simultaneously, sequentially, or contemporaneously therapeutically effective amounts of:

(i) a PDE1 Inhibitor of the invention, in free or pharmaceutically acceptable salt form; and (ii) an antipsychotic, e.g., Typical antipsychotics, e.g., Butyrophenones, e.g. Haloperidol (Haldol, Serenace), Droperidol (Droleptan);

Phenothiazines, e.g., Chlorpromazine (Thorazine, Largactil), Fluphenazine (Prolixin), Perphenazine (Trilafon), Prochlorperazine (Compazine), Thioridazine (Mellaril, Melleril), Trifluoperazine (Stelazine), Mesoridazine, Periciazine, Promazine, Triflupromazine (Vesprin), Levomepromazine (Nozinan), Promethazine (Phenergan), Pimozide (Orap);

Thioxanthenes, e.g., Chlorprothixene, Flupenthixol (Depixol, Fluanxol), Thiothixene (Navane), Zuclopenthixol (Clopixol, Acuphase);

Atypical antipsychotics, e.g.,

Clozapine (Clozaril), Olanzapine (Zyprexa), Risperidone (Risperdal), Quetiapine (Seroquel), Ziprasidone (Geodon), Amisulpride (Solian), Paliperidone (Invega), Aripiprazole (Abilify), Bifeprunox; norclozapine, in free or pharmaceutically acceptable salt form, to a patient in need thereof.

In a particular embodiment, the Compounds of the Invention are particularly useful for the treatment or prophylaxis of schizophrenia.

Compounds of the Invention, in free or pharmaceutically acceptable salt form, are particularly useful for the treatment of Parkinson's disease, schizophrenia, narcolepsy, glaucoma and female sexual dysfunction.

In still another aspect, the invention provides a method of lengthening or enhancing growth of the eyelashes by administering an effective amount of a prostaglandin analogue, e.g., bimatoprost, concomitantly, simultaneously or sequentially with an effective amount of a PDE1 inhibitor of the Invention, in free or pharmaceutically acceptable salt form, to the eye of a patient in need thereof.

In yet another aspect, the invention provides a method for the treatment or prophylaxis of traumatic brain injury comprising administering a therapeutically effective amount of a PDE1 Inhibitor of the Invention, e.g., a compound according to any of Formula V or 1.1-1.14, in free or pharmaceutically acceptable salt form, to a patient in need thereof. Traumatic brain injury (TBI) encompasses primary injury as well as secondary injury, including both focal and diffuse brain injuries. Secondary injuries are multiple, parallel, interacting and interdependent cascades of biological reactions arising from discrete subcellular processes (e.g., toxicity due to reactive oxygen species, overstimulation of glutamate receptors, excessive influx of calcium and inflammatory upregulation) which are caused or exacerbated by the inflammatory response and progress after the initial (primary) injury.

The present invention also provides (i) a Compound of the Invention, e.g., a compound according to any of Formula V or 1.1-1.14, as hereinbefore described, in free or pharmaceutically acceptable salt form for example for use in any method or in the treatment of any disease or condition as hereinbefore set forth, (ii) the use of a Compound of the Invention, e.g., a compound according to any of Formula V or 1.1-1.14, as hereinbefore described, in free or pharmaceutically acceptable salt form, (in the manufacture of a medicament) for treating any disease or condition as hereinbefore set forth, (iii) a pharmaceutical composition comprising a Compound of the Invention, e.g., a compound according to any of Formula V or 1.1-1.14, as hereinbefore described, in free or pharmaceutically acceptable salt form, in combination or association with a pharmaceutically acceptable diluent or carrier, and (iv) a pharmaceutical composition comprising a Compound of the Invention, e.g., a compound according to any of Formula V or 1.1-1.14, as hereinbefore described, in free or pharmaceutically acceptable salt form, in combination or association with a pharmaceutically acceptable diluent or carrier for use in the treatment of any disease or condition as hereinbefore set forth.

Therefore, the invention provides use of a Compound of the Invention, e.g., a compound according to any of Formula V or 1.1-1.14, as hereinbefore described, in free or pharmaceutically acceptable salt form, or a Compound of the Invention in a pharmaceutical composition form (in the manufacture of a medicament) for the treatment or prophylactic treatment of any one or more of the following diseases: Parkinson's disease, restless leg, tremors, dyskinesias, Huntington's disease, Alzheimer's disease, and/or drug-induced movement disorders; depression, attention deficit disorder, attention deficit hyperactivity disorder, bipolar illness, anxiety, sleep disorder, narcolepsy, cognitive impairment, e.g., cognitive impairment of schizophrenia, dementia, Tourette's syndrome, autism, fragile X syndrome, psychostimulant withdrawal, and/or drug addiction; cerebrovascular disease, stroke, congestive heart disease, hypertension, pulmonary hypertension, e.g., pulmonary arterial hypertension, and/or sexual dysfunction; asthma, chronic obstructive pulmonary disease, and/or allergic rhinitis, as well as autoimmune and inflammatory diseases; and/or female sexual dysfunction, exercise amenorrhoea, anovulation, menopause, menopausal symptoms, hypothyroidism, pre-menstrual syndrome, premature labor, infertility, irregular menstrual cycles, abnormal uterine bleeding, osteoporosis, multiple sclerosis, prostate enlargement, prostate cancer, hypothyroidism, and/or estrogen-induced endometrial hyperplasia and/or carcinoma; and/or any disease or condition characterized by low levels of cAMP and/or cGMP (or inhibition of cAMP and/or cGMP signaling pathways) in cells expressing PDE1, and/or by reduced dopamine D1 receptor signaling activity; and/or any disease or condition that may be ameliorated by the enhancement of progesterone signaling.

The invention also provides use of a Compound of the Invention, in free or pharmaceutically acceptable salt form, (the manufacture of a medicament) for the treatment or prophylactic treatment of any one or more of:

a) glaucoma, elevated intraocular pressure, b) psychosis, for example, any conditions characterized by psychotic symptoms such as hallucinations, paranoid or bizarre delusions, or disorganized speech and thinking, e.g., schizophrenia, schizoaffective disorder, schizophreniform disorder, psychotic disorder, delusional disorder, and mania, such as in acute manic episodes and bipolar disorder, c) traumatic brain injury, and/or d) central and peripheral degenerative disorders particularly those with inflammatory components.

The phrase "Compounds of the Invention" or "PDE 1 inhibitors of the Invention" encompasses any and all of the compounds disclosed herewith, e.g., a Compound of Formula V or 1.1-1.14.

The words "treatment" and "treating" are to be understood accordingly as embracing prophylaxis and treatment or amelioration of symptoms of disease as well as treatment of the cause of the disease.

For methods of treatment, the word "therapeutically effective amount" as used herein refers to an amount of a drug (e.g., a PDE1 inhibitor) sufficient to treat or ameliorate the pathological effects a CNS or PNS disease, disorder, or injury. For example, a therapeutically effective amount of a PDE1 inhibitor may be an amount sufficient to, e.g., increase intracellular levels of cAMP or cGMP, decrease intracellular levels of calcium, and/or increase neuroregeneration. Where relevant, a therapeutically effective amount may also be the amount of a PDE1 inhibitor necessary to slow or prevent the development of CNS or PNS disease or disorder.

The term "patient" or "subject" refers to human or non-human (i.e., animal) patient. In a particular embodiment, the invention encompasses both human and nonhuman patients. In another embodiment, the invention encompasses nonhuman patients. In other embodiment, the term encompasses human patients.

The term "control subject" as used herein, refers to any human or nonhuman organism that does not have and/or is not suspected of having a CNS or PNS disorder, syndrome, disease, condition and/or symptom. The term "reference standard" as used herein, refers to the prior measurement and obtaining of results in a control subject or population of control subjects. In another aspect, the term "reference standard" refers to the prior measurement and obtaining of results in a patient prior to his or her development of a CNS or PNS disorder, syndrome, disease, condition and/or symptom.

The term "biological sample" as used herein, may include any sample comprising biological material obtained from, e.g., an organism, body fluid, waste product, cell or part of a cell thereof, cell line, biopsy, tissue culture or other source containing a intracellular calcium, cAMP, or cGMP levels.

A "neurogenic agent" is defined as a chemical agent or reagent that can promote, stimulate, or otherwise increase the amount or degree or nature of neurogenesis in vivo or ex vivo or in vitro, relative to the amount, degree, or nature of neurogenesis in the absence of the agent or reagent.

A "CNS injury" as used herein may include, e.g., damage to retinal ganglion cells, a traumatic brain injury, a stroke-related injury, a cerebral aneurism-related injury, a spinal cord injury or trauma, including monoplegia, diplegia, paraplegia, hemiplegia and quadriplegia, a neuroproliferative disorder, or neuropathic pain syndrome. A "PNS injury" as used herein may include, e.g., damage to the spinal or cranial nerves, wherein that damage may include a lesion or some acute or chronic trauma.

Compounds of the Invention, (e.g., any of Formula V or 1.1-1.14) as hereinbefore described, in free or pharmaceutically acceptable salt form, may be used as a sole therapeutic agent, but may also be used in combination with or for co-administration with other active agents.

Dosages employed in practicing the present invention will of course vary depending, e.g. on the particular disease or condition to be treated, the particular Compound of the Invention used, the mode of administration, and the therapy desired. Compounds of the Invention may be administered by any suitable route, including orally, parenterally, transdermally, or by inhalation, but are preferably administered orally. In general, satisfactory results, e.g. for the treatment of diseases as hereinbefore set forth are indicated to be obtained on oral administration at dosages of the order from about 0.01 to 2.0 mg/kg. In larger mammals, for example humans, an indicated daily dosage for oral administration will accordingly be in the range of from about 0.75 to 150 mg, conveniently administered once, or in divided doses 2 to 4 times, daily or in sustained release form. Unit dosage forms for oral administration thus for example may comprise from about 0.2 to 75 or 150 mg, e.g. from about 0.2 or 2.0 to 50, 75 or 100 mg of a Compound of the Invention, together with a pharmaceutically acceptable diluent or carrier therefor.

Pharmaceutical compositions comprising Compounds of the Invention may be prepared using conventional diluents or excipients and techniques known in the galenic art. Thus oral dosage forms may include tablets, capsules, solutions, suspensions and the like.

EXAMPLES

Example 1

7,8-Dihydro-2-(4-(pyridine-2-yl)benzyl)-3-(4-fluorophenylamino)-5,7,7-trimethyl-[2H]-imidazo-[1,2-a]pyrazolo[4,3-e]pyrimidin-4(5H)-one

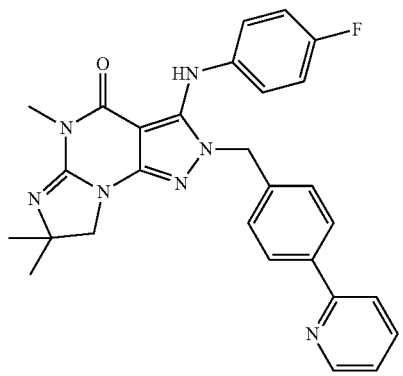 [SMILES: CN1C(=O)c2c(nn(Cc3ccc(-c4ccccn4)cc3)c2Nc2ccc(F)cc2)N2CC(C)(C)N=C12]

(a) 7-(4-Methoxybenzyl)-5-methyl-2-(4-(pyridin-2-yl)benzyl)-2H-pyrazolo[3,4-d]pyrimidine-4,6(5H,7H)-dione A suspension of 7-(4-methoxybenzyl)-5-methyl-2H-pyrazolo[3,4-d]pyrimidine-4,6(5H,7H)-dione (8.43 g, 29.4 mmol), 2-(4-(chloromethyl)phenyl)-pyridine (6.0 g, 29.4 mmol) and $K_2CO_3$ (4.07 g, 29.4 mmol) in DMF (100 mL) is stirred at room temperature overnight. Solvent is removed under reduced pressure. The obtained residue is treated with water (150 mL) and hexanes (25 mL). The mixture is stirred at room temperature for an hour, and then filtered. The filter cake is washed with water three times (3×50 mL), and then dried under vacuum to give 13 g of crude product (yield: 97%), which is used in the next step without further purification. MS (ESI) m/z 454.2 $[M+H]^+$.

(b) 5-Methyl-2-(4-(pyridin-2-yl)benzyl)-2H-pyrazolo[3,4-d]pyrimidine-4,6(5H,7H)-dione TFA (50 mL) is added into a suspension of 7-(4-Methoxybenzyl)-5-methyl-2-(4-(pyridin-2-yl)benzyl)-2H-pyrazolo

[3,4-d]pyrimidine-4,6(5H,7H)-dione (13 g, 28.7 mmol) in methylene chloride (80 mL) to give a tan solution, and then TFMSA (4 mL) is added. The reaction mixture is stirred at room temperature overnight. Solvents are removed under reduced pressure. The obtained residue is treated with water (150 mL), cooled to 0° C., and then adjusted to pH 8-9 with 28% ammonium hydroxide (approx. 35 mL). After filtration, the obtained solids are washed with water three times (3×50 mL), and then dried under vacuum to give 12.8 g of crude product (crude yield: 134%), which is used in the next step without further purification. MS (ESI) m/z 334.1 [M+H]$^+$.

(c) 6-Chloro-5-methyl-2-(4-(pyridin-2-yl)benzyl)-2H-pyrazolo[3,4-d]pyrimidin-4(5H)-one 5-Methyl-2-(4-(pyridin-2-yl)benzyl)-2H-pyrazolo[3,4-d]pyrimidine-4,6(5H,7H)-dione (8.5 g, 25.5 mmol) is suspended in POCl$_3$ (300 mL), and then slowly heated to reflux. After the mixture is refluxed for 30 h, POCl$_3$ is removed under reduced pressure. The obtained residue is treated with water (300 mL), cooled to 0° C., and then adjusted to pH 8-9 with 28% ammonium hydroxide (approx. 30 mL). After filtration, the obtained solids are washed with water five times (5×50 mL), and then dried under vacuum to give 8.6 g of crude product (crude yield: 96%), which is used in the next step without further purification. MS (ESI) m/z 352.1 [M+H]$^+$.

(d) 6-(1-Hydroxy-2-methylpropan-2-ylamino)-5-methyl-2-(4-(pyridin-2-yl)benzyl)-2H-pyrazolo[3,4-d]pyrimidin-4(5H)-one A mixture of 6-Chloro-5-methyl-2-(4-(pyridin-2-yl)benzyl)-2H-pyrazolo[3,4-d]pyrimidin-4(5H)-one (4.0 g, 11 mmol), 2-amino-2-methylpropan-1-ol (6.5 mL, 71 mmol) and DIPEA (3.4 mL, 20 mmol) in DMA (20 mL) is heated at 130° C. for an hour. Solvent is removed under reduced pressure. The obtained residue is treated with water (200 mL). After filtration, the filter cake is washed with water twice (2×50 mL), and then dried under vacuum to give 3.7 g of crude product (crude yield: 80%), which is used in the next step without further purification. MS (ESI) m/z 405.2 [M+H]$^+$.

(e) 7,8-Dihydro-2-(4-(pyridin-2-yl)benzyl)-5,7,7-trimethyl-[2H]-imidazo-[1,2-a]pyrazolo[4,3-e]pyrimidin-4(5H)-one Thionyl chloride (756 μL, 10.4 mmol) is added dropwise to a solution of crude 6-(1-hydroxy-2-methylpropan-2-ylamino)-5-methyl-2-(4-(pyridin-2-yl)benzyl)-2H-pyrazolo[3,4-d]pyrimidin-4(5H)-one (4.2 g, 10.4 mmol) in DMF (84 mL). The reaction mixture is stirred at room temperature for 20 min. Water (5 mL) is added to quench the reaction. Solvents are removed under reduced pressure. The obtained residue is treated with methylene chloride, and then washed with 5% NaHCO$_3$ aqueous solution three times. The organic phase is evaporated to dryness to give 6.1 g of crude product (crude yield: 152%), which is used in the next step without further purification. MS (ESI) m/z 387.2 [M+H]$^+$.

(f) 7,8-Dihydro-2-(4-(pyridin2-yl)benzyl)-3-chloro-5,7,7-trimethyl-[2H]-imidazo-[1,2-a]pyrazolo[4,3-e]pyrimidin-4(5H)-one 1.0M LiHMDS (55.4 mL, 55.4 mmol) in THF is added dropwise to a solution of crude 7,8-dihydro-2-(4-(pyridin-2-yl)benzyl)-5,7,7-trimethyl-[2H]-imidazo-[1,2-a]pyrazolo[4,3-e]pyrimidin-4(5H)-one (4.6 g, 11.9 mmol) and hexachloroethane (2.58 g, 10.9 mmol) in methylene chloride (130 mL) at 0° C. The reaction mixture is stirred at 0° C. for 30 min, and then quenched with water (100 mL) and methylene chloride (150 mL). The organic phase is washed with water three times (3×70 mL), and then evaporated to dryness. The obtained crude product is purified on a neutral aluminum oxide column to give 1.5 g of pure product (HPLC purity: 96%; yield: 30%). MS (ESI) m/z 421.1 [M+H]$^+$.

(g) 7,8-Dihydro-2-(4-(pyridin2-yl)benzyl)-3-(4-fluorophenylamino)-5,7,7-trimethyl-[2H]-imidazo-[1,2-a]pyrazolo[4,3-e]pyrimidin-4(5H)-one 7,8-Dihydro-2-(4-(pyridin2-yl)benzyl)-3-chloro-5,7,7-trimethyl-[2H]-imidazo-[1,2-a]pyrazolo[4,3-e]pyrimidin-4(5H)-one (550 mg, 1.31 mmol), 4-fluorobenzenamine (125 μL, 1.31 mmol) and potassium carbonate (361 mg, 2.61 mmol) in tert-amyl alcohol (3 mL) are degassed with argon and then Xantphos (15 mg, 0.026 mmol) and Pd$_2$(dba)$_3$ (12 mg, 0.013 mmol) are added. The suspension is degassed again, and then slowly heated to 110° C. The reaction mixture is stirred at 110° C. under argon overnight. Another batch of Pd$_2$(dba)$_3$ (12 mg) and Xantphos (15 mg) is added. The reaction is heated at 110° C. for additional 24 h for complete conversion. After routine workup, the crude product is purified by silica-gel column chromatography to give 352 mg of final product as a beige solid (HPLC purity: 97.4%; yield: 54%). $^1$H NMR (500 MHz, Chloroform-d) δ 8.68 (dt, J=4.7, 1.3 Hz, 1H), 7.88 (d, J=8.3 Hz, 2H), 7.74 (td, J=7.7, 1.8 Hz, 1H), 7.68 (d, J=8.0 Hz, 2H), 7.23 (ddd, J=7.4, 4.8, 1.2 Hz, 1H), 7.06 (d, J=8.3 Hz, 2H), 7.00-6.93 (m, 2H), 6.94-6.87 (m, 2H), 6.79 (s, 1H), 4.90 (s, 2H), 3.71 (s, 2H), 3.35 (s, 3H), 1.40 (s, 6H). MS (ESI) m/z 496.2 [M+H]$^+$.

The compound of Example 1 shows good selectivity for PDE1 and inhibits PDE activity at an IC$_{50}$ value of equal to or less than 5 nM.

Example 2

7,8-Dihydro-2-(4-(6-Fluoropyridin-2-yl)benzyl)-3-(4-fluorophenylamino)-5,7,7-trimethyl-[2H]-imidazo-[1,2-a]pyrazolo[4,3-e]pyrimidin-4(5H)-one

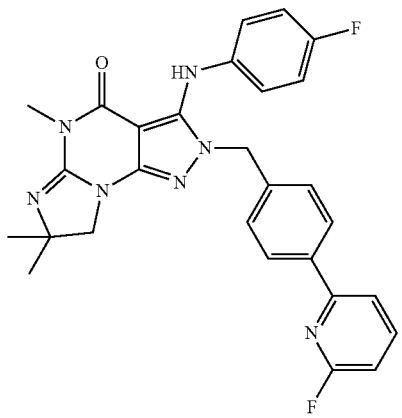 [SMILES: CN1C(=O)c2c(nn(Cc3ccc(-c4cccc(F)n4)cc3)c2Nc2ccc(F)cc2)N2CC(C)(C)N=C12]

The synthesis method is analogous to example 1 wherein 2-(4-(chloromethyl)phenyl)-6-fluoropyridine is added in step (a) instead of 2-(4-(chloromethyl)phenyl)-pyridine.

Final product is obtained as a off-white solid (HPLC purity: 99%). ¹H NMR (500 MHz, Chloroform-d) δ 7.89 (d, J=8.4 Hz, 2H), 7.83 (q, J=8.0 Hz, 1H), 7.58 (dd, J=7.5, 2.3 Hz, 1H), 7.05 (d, J=8.3 Hz, 2H), 7.00-6.84 (m, 6H), 4.91 (s, 2H), 3.76 (s, 2H), 3.39 (s, 3H), 1.47 (s, 6H). MS (ESI) m/z 514.3 [M+H]⁺

Example 3

7,8-Dihydro-2-(4-(pyridine-2-yl)benzyl)-3-(3,4-difluorophenylamino)-5,7,7-trimethyl-[2H]-imidazo-[1,2-a]pyrazolo[4,3-e]pyrimidin-4(5H)-one

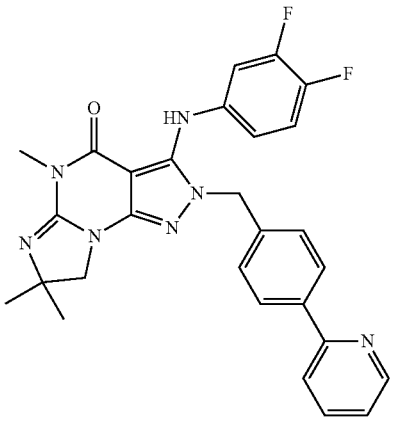 [SMILES: CN1C(=O)c2c(nn(Cc3ccc(-c4ccccn4)cc3)c2Nc2ccc(F)c(F)c2)N2CC(C)(C)N=C12]

(a) 2-(4-Bromobenzyl)-7,8-dihydro-5,7,7-trimethyl-[2H]-imidazo-[1,2-a]pyrazolo[4,3-e]pyrimidin-4(5H)-one The title compound is synthesized using the procedure analogous to the one described from step (a) to step (e) of Example 1 wherein 1-bromo-4-(bromomethyl)benzene was added in step (a) instead of 2-(4-(chloromethyl)phenyl)pyridine. MS (ESI) m/z 388.1 [M+H]⁺.

(b) 2-(4-Phenoxybenzyl)-7,8-dihydro-5,7,7-trimethyl-[2H]-imidazo-[1,2-a]pyrazolo[4,3-e]pyrimidin-4(5H)-one 2-(4-Bromobenzyl)-7,8-dihydro-5,7,7-trimethyl-[2H]-imidazo-[1,2-a]pyrazolo[4,3-e]pyrimidin-4(5H)-one (118 g, 304 mmol) is added to a suspension of phenol (57 g, 606 mmol) and cesium carbonate (200 g, 614 mmol) in NMP (900 mL), followed by 2,2,6,6-tetramethylheptane-3,5-dione (7 mL, 33.5 mmol) and CuCl (15 g, 152 mmol). The reaction mixture is heated at 120° C. under nitrogen atmosphere for 10 h. After the completion of the reaction, the mixture is diluted with water (4 L), and then extracted with ethyl acetate. The combined organic phase is evaporated to dryness. The obtained crude product is purified by silica gel column chromatography to give 103 g of product (yield: 84%). MS (ESI) m/z 402.2 [M+H]⁺.

(c) 7,8-Dihydro-5,7,7-trimethyl-[2H]-imidazo-[1,2-a]pyrazolo[4,3-e]pyrimidin-4(5H)-one TFA (600 mL) is added to a suspension of 2-(4-phenoxybenzyl)-7,8-dihydro-5,7,7-trimethyl-[2H]-imidazo-[1,2-a]pyrazolo[4,3-e]pyrimidin-4(5H)-one (103 g, 257 mmol) in methylene chloride (210 mL) to give a tan solution, and then TFMSA (168 mL) is added. The reaction mixture is stirred at room temperature until the starting material disappears. The reaction mixture is poured into cold water (3 L). After filtration, the filter cake is washed with water twice, and then basified with ammonium hydroxide aqueous solution, followed by adding ethyl acetate with stirring. The precipitated solids are filtered, washed successively with water three times, ethyl acetate twice and methanol once, and then dried under vacuum to give 45 g of product (yield: 80%). MS (ESI) m/z 220.2 [M+H]⁺.

(d) 7,8-Dihydro-2-(4-(pyridin-2-yl)benzyl)-5,7,7-trimethyl-[2H]-imidazo-[1,2-a]pyrazolo[4,3-e]pyrimidin-4(5H)-one A suspension of 7,8-dihydro-5,7,7-trimethyl-[2H]-imidazo-[1,2-a]pyrazolo[4,3-e]pyrimidin-4(5H)-one (1.5 g, 6.84 mmol), 2-(4-(bromomethyl)phenyl)pyridine (1.7 g, 6.84 mmol) and K₂CO₃ (2.83 g, 20.5 mmol) in DMF (60 mL) is stirred at room temperature for 2-3 days. Solvent is removed under reduced pressure. The obtained residue is treated with water (100 mL), sonicated and then filtered. The filter cake is dried under vacuum to give 2.19 g of crude product (yield: 83%), which is used in the next step without further purification. MS (ESI) m/z 387.1 [M+H]⁺.

(e) 7,8-Dihydro-2-(4-(pyridine-2-yl)benzyl)-3-chloro-5,7,7-trimethyl-[2H]-imidazo-[1,2-a]pyrazolo[4,3-e]pyrimidin-4(5H)-one 1.0M LiHMDS (3.0 mL, 3.0 mmol) in THF is added dropwise to a solution of crude 7,8-dihydro-2-(4-(pyridin2-yl)benzyl)-5,7,7-trimethyl-[2H]-imidazo-[1,2-a]pyrazolo[4,3-e]pyrimidin-4(5H)-one (1.16 g, 3.0 mmol) and hexachloroethane (2.13 g, 9.0 mmol) in methylene chloride (30 mL). The reaction mixture is stirred at room temperature for 90 minutes, and is then quenched with cold water (200 mL). The mixture is extracted with methylene chloride three times (50 mL×3), and the combined organic phase was washed with brine (30 mL), and then evaporated to dryness under reduced pressure. The obtained residue is purified on a neutral alumina oxide column to give 960 mg of pure product as an off-white solid (HPLC purity: 96.8%; yield: 76%). MS (ESI) m/z 421.2 [M+H]⁺.

(f) 7,8-Dihydro-2-(4-(pyridine-2-yl)benzyl)-3-(3,4-difluorophenylamino)-5,7,7-trimethyl-[2H]-imidazo-[1,2-a]pyrazolo[4,3-e]pyrimidin-4(5H)-one 7,8-Dihydro-2-(4-(pyridin2-yl)benzyl)-3-chloro-5,7,7-trimethyl-[2H]-imidazo-[1,2-a]pyrazolo[4,3-e]pyrimidin-4(5H)-one (230 mg, 0.546 mmol), 3,4-difluorobenzenamine (106 mg, 0.821 mmol) and potassium carbonate (300 mg, 2.17 mmol) in tert-amyl alcohol (2.8 mL) are degassed with argon, and then Xantphos (26 mg, 0.045 mmol) and Pd₂(dba)₃ (20 mg, 0.022 mmol) are added. The suspension is degassed again, and then heated to 110° C. The reaction mixture is stirred at 110° C. under argon overnight. After routine workup, the crude product is purified on a basic alumina oxide column to give 194 mg of final product as a beige solid (HPLC purity: 99%; yield: 69%). ¹H NMR (500 MHz, Chloroform-d) δ 8.69 (d, J=4.5 Hz, 1H), 7.88 (d, J=8.2 Hz, 2H), 7.76 (td, J=7.8, 1.6 Hz, 1H), 7.67 (d, J=7.9 Hz, 1H), 7.26-7.17 (m, 2H), 7.15 (d, J=8.2 Hz, 2H), 7.03 (m, 1H), 6.69 (m, 1H), 6.60 (m, 1H), 5.05 (s, 2H), 3.79 (s, 2H), 3.29 (s, 3H), 1.47 (s, 6H). MS (ESI) m/z 514.2 [M+H]⁺.

Example 4

7,8-Dihydro-2-(4-(pyridin2-yl)benzyl)-3-(4-fluoro-3-methylphenylamino)-5,7,7-trimethyl-[2H]-imidazo-[1,2-a]pyrazolo[4,3-e]pyrimidin-4(5H)-one

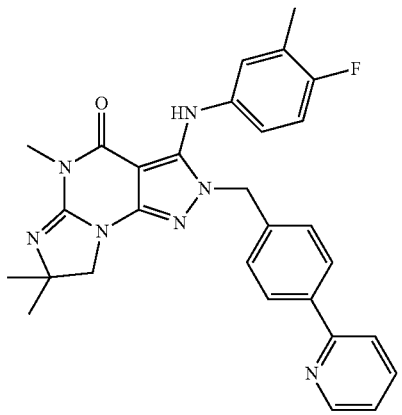 [SMILES: Cc1cc(Nc2c3c(nn2Cc2ccc(-c4ccccn4)cc2)N2CC(C)(C)N=C2N(C)C3=O)ccc1F]

The synthesis method is analogous to example 3 wherein 4-fluoro-3-methylbenzenamine was added in step (f) instead of 3,4-difluorobenzenamine. Final product is obtained as an off-white solid (HPLC purity: 97%). ¹H NMR (500 MHz, Chloroform-d) δ 8.70 (ddd, J=4.8, 1.9, 1.0 Hz, 1H), 7.86 (d, J=8.3 Hz, 2H), 7.77 (td, J=7.7, 1.9 Hz, 1H), 7.68 (d, J=8.0 Hz, 1H), 7.26 (m, 1H), 7.06 (d, J=8.3 Hz, 2H), 6.97-6.86 (m, 2H), 6.81-6.69 (m, 2H), 4.91 (s, 2H), 3.81 (s, 2H), 3.40 (s, 3H), 2.13 (d, J=1.4 Hz, 3H), 1.49 (s, 6H). MS (ESI) m/z 510.2 [M+H]+

Example 5

7,8-Dihydro-2-(4-(5-fluoropyridin2-yl)benzyl)-3-ethyl-5,7,7-trimethyl-[2H]-imidazo-[1,2-a]pyrazolo[4,3-e]pyrimidin-4(5H)-one

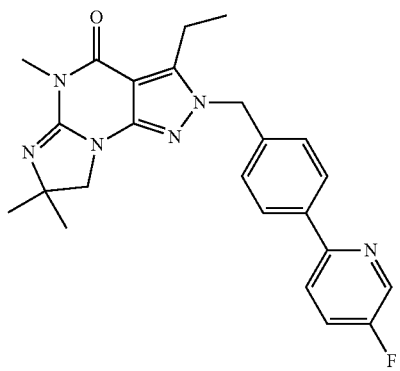 [SMILES: CCc1c2c(nn1Cc1ccc(-c3ccc(F)cn3)cc1)N1CC(C)(C)N=C1N(C)C2=O]

(a) 7,8-Dihydro-2-(4-(5-fluoropyridin2-yl)benzyl)-3-chloro-5,7,7-trimethyl-[2H]-imidazo-[1,2-a]pyrazolo[4,3-e]pyrimidin-4(5H)-one The title compound is prepared using the procedure analogous to the one described in steps (a) to (f) of Example 1 wherein 2-(4-(chloromethyl)phenyl)-5-fluoropyridine was added in step (a) instead of 2-(4-(chloromethyl)phenyl)-pyridine. MS (ESI) m/z 439.2 [M+H]⁺.

(b) 7,8-Dihydro-2-(4-(5-fluoropyridin2-yl)benzyl)-3-ethyl-5,7,7-trimethyl-[2H]-imidazo-[1,2-a]pyrazolo[4,3-e]pyrimidin-4(5H)-on Ethylmagnesium bromide (3.0 M in ether, 3 mL) is added dropwise to a reaction vial containing ZnCl₂ (1.2 g, 8.8 mmol) at 0° C. under argon. The mixture is stirred at room temperature for 20 min, and is then cooled to −78° C. 9-Methoxy-9-borabicyclo[3.3.1]nonane (1.0 M in hexanes, 8 mL) is added dropwise. After the completion of the addition, the mixture is stirred at room temperature for 40 min. 7,8-Dihydro-2-(4-(5-fluoropyridin2-yl)benzyl)-3-chloro-5,7,7-trimethyl-[2H]-imidazo-[1,2-a]pyrazolo[4,3-e]pyrimidin-4(5H)-one (352 mg, 0.8 mmol) in anhydrous DMF (15 mL) is slowly added to the mixture, followed by 2-dicyclohexylphosphino-2',6'-dimethoxybiphenyl (S-Phos, 38 mg) and palladium acetate (13 mg). The reaction vial is sealed and stirred at room temperature for 30 min, and is then heated at 100° C. for 4 days. The mixture is diluted with water (150 mL), and then extracted with dichloromethane (60 mL×3). The combined organic phase is evaporated to dryness under reduced pressure. The residue is purified by a with a semi-preparative HPLC system equipped with a reversed-phase C18 column using a gradient of 0-26% acetonitrile in water containing 0.1% formic acid over 16 min to give 177 mg of product as a pale yellow solid (HPLC purity: 99.5%; yield: 51%). ¹H NMR (500 MHz, Chloroform-d) δ 8.53 (d, J=2.9 Hz, 1H), 7.92 (d, J=8.3 Hz, 2H), 7.69 (dd, J=8.8, 4.2 Hz, 1H), 7.47 (td, J=8.4, 2.9 Hz, 1H), 7.25 (d, J=9.0 Hz, 2H), 5.29 (s, 2H), 3.73 (s, 2H), 3.41 (s, 3H), 2.95 (q, J=7.6 Hz, 2H), 1.42 (s, 6H), 1.18 (t, J=7.5 Hz, 3H). MS (ESI) m/z 433.3 [M+H]⁺.

Example 6

7,8-Dihydro-2-(4-(6-fluoropyridin2-yl)benzyl)-3-ethyl-5,7,7-trimethyl-[2H]-imidazo-[1,2-a]pyrazolo[4,3-e]pyrimidin-4(5H)-one

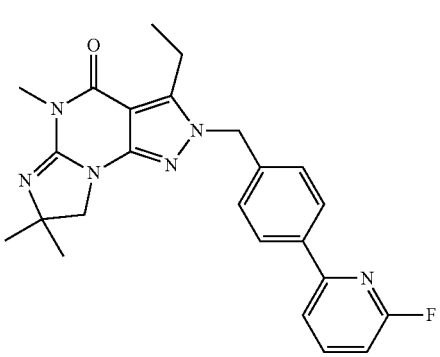 [SMILES: CCc1c2c(nn1Cc1ccc(-c3cccc(F)n3)cc1)N1CC(C)(C)N=C1N(C)C2=O]

The title compound is prepared using the procedure analogous to the one described in Example 5 wherein 2-(4-(chloromethyl)phenyl)-6-fluoropyridine was added in step (a) instead of 2-(4-(chloromethyl)phenyl)-5-fluoropyridine. ¹H NMR (400 MHz, Chloroform-d) δ 7.98 (d, J=8.4 Hz, 2H), 7.84 (m, 1H), 7.59 (dd, J=7.5, 2.4 Hz, 2H), 7.25 (d, J=8.4 Hz, 3H), 6.87 (dd, J=8.1, 3.0 Hz, 1H), 5.28 (s, 2H), 3.71 (s, 2H), 3.38 (s, 3H), 2.94 (q, J=7.5 Hz, 2H), 1.40 (s, 6H), 1.17 (t, J=7.5 Hz, 3H). MS (ESI) m/z 433.2 [M+H]+.

The compound of Example 5 shows good selectivity for PDE1 and inhibits PDE activity at an $IC_{50}$ value of equal to or less than 30 nM.

Example 7

7,8-Dihydro-2-(4-(5-fluoropyridin2-yl)benzyl)-3-propyl-5,7,7-trimethyl-[2H]-imidazo-[1,2-a]pyrazolo[4,3-e]pyrimidin-4(5H)-one

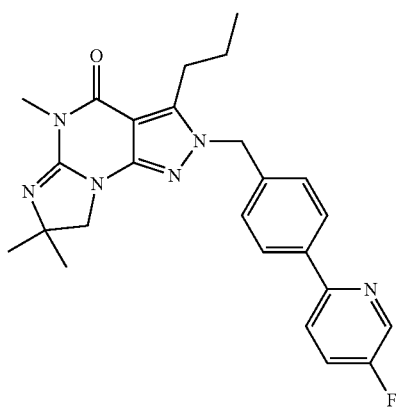 [SMILES: CCCc1c2c(nn1Cc1ccc(-c3ccc(F)cn3)cc1)N1CC(C)(C)N=C1N(C)C2=O]

The title compound is prepared using the procedure analogous to the one described in Example 5 wherein propylmagnesium bromide was added in step (b) instead of ethylmagnesium bromide. MS (ESI) m/z 447.2 [M+H]+.

The compound of Example 7 shows good selectivity for PDE1 and inhibits PDE activity at an $IC_{50}$ value of equal to or less than 15 nM.

Example 8

7,8-Dihydro-2-(4-(6-fluoropyridin2-yl)benzyl)-3-propyl-5,7,7-trimethyl-[2H]-imidazo-[1,2-a]pyrazolo[4,3-e]pyrimidin-4(5H)-one

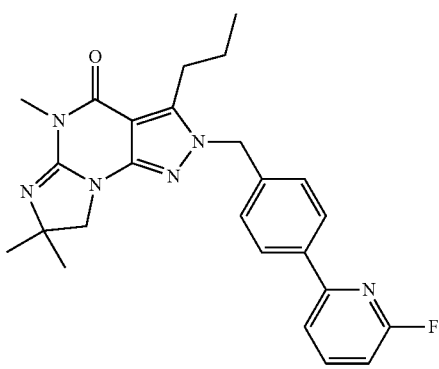 [SMILES: CCCc1c2c(nn1Cc1ccc(-c3cccc(F)n3)cc1)N1CC(C)(C)N=C1N(C)C2=O]

The title compound is prepared using the procedure analogous to the one described in Example 5 wherein propylmagnesium bromide was added in step (b) instead of ethylmagnesium bromide, and 2-(4-(chloromethyl)phenyl)-6-fluoropyridine was added in step (a) instead of 2-(4-(chloromethyl)phenyl)-5-fluoropyridine. MS (ESI) m/z 447.2 [M+H]+.

Example 9

7,8-Dihydro-2-(4-chlorobenzyl)-3-(4-fluorophenylamino)-5,7,7-trimethyl-[2H]-imidazo-[1,2-a]pyrazolo[4,3-e]pyrimidin-4(5H)-one

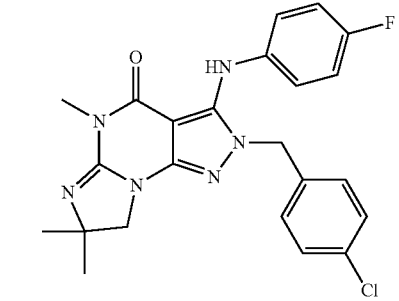 [SMILES: CN1C(=O)c2c(nn(Cc3ccc(Cl)cc3)c2Nc2ccc(F)cc2)N2CC(C)(C)N=C12]

The title compound is prepared using the procedure analogous to the one described in Example 1 wherein 1-chloro-4-(chloromethyl)benzene was added in step (a) instead of 2-(4-(chloromethyl)phenyl)-pyridine. MS (ESI) m/z 453.2 [M+H]+

The compound of Example 9 shows good selectivity for PDE1 and inhibits PDE activity at an $IC_{50}$ value of equal to or less than 5 nM.

Example 10: Measurement of PDEIB Inhibition in Vitro Using IMAP Phosphodiesterase Assay Kit Phosphodiesterase I B (PDEIB) is a calcium/calmodulin dependent phosphodiesterase enzyme that converts cyclic guanosine monophosphate (cGMP) to 5'-guanosine monophosphate (5'-GMP). PDEIB can also convert a modified cGMP substrate, such as the fluorescent molecule cGMP-fluorescein, to the corresponding GMP-fluorescein. The generation of GMP-fluorescein from cGMP-fluorescein can be quantitated, using, for example, the IMAP (Molecular Devices, Sunnyvale, Calif.) immobilized-metal affinity particle reagent.

Briefly, the IMAP reagent binds with high affinity to the free 5'-phosphate that is found in GMP-fluorescein and not in cGMP-fluorescein. The resulting GMP-fluorescein-IMAP complex is large relative to cGMP-5 fluorescein. Small fluorophores that are bound up in a large, slowly tumbling, complex can be distinguished from unbound fluorophores, because the photons emitted as they fluoresce retain the same polarity as the photons used to excite the fluorescence.

In the phosphodiesterase assay, cGMP-fluorescein, which cannot be bound to IMAP, and therefore retains little fluorescence polarization, is converted to GMPfluorescein, which, when bound to IMAP, yields a large increase in fluorescence polarization (mp). Inhibition of phosphodiesterase, therefore, is detected as a decrease in mp.
Enzyme Assay Materials: All chemicals are available from Sigma-Aldrich (St. Louis, Mo.) except for IMAP reagents (reaction buffer, binding buffer, FL-GMP and IMAP beads), which are available from Molecular Devices (Sunnyvale, Calif.).

Assay: The following phosphodiesterase enzymes may be used: 3',5'-cyclic-nucleotide specific bovine brain phosphodiesterase (Sigma, St. Louis, Mo.) (predominantly PDE1B) and recombinant full length human PDE1 A and PDE1B (r-hPDE1 A and r-hPDE1B respectively) which may be produced e.g., in HEK or SF9 cells by one skilled in the art. The PDE1 enzyme is reconstituted with 50% glycerol to 2.5 U/mL. One unit of enzyme will hydrolyze 1.0 μmol of 3',5'-cAMP to 5'-AMP per min at pH 7.5 at 30° C. One part enzyme is added to 1999 parts reaction buffer (30 μM $CaCl_2$, 10 U/mL of calmodulin (Sigma P2277), 10 mM Tris-HCl pH 7.2, 10 mM $MgCl_2$, 0.1% BSA, 0.05% $NaN_3$) to yield a final concentration of 1.25 mU/mL. 99 μL of diluted enzyme solution is added into each well in a flat bottom 96-well polystyrene plate to which 1 μL of test compound dissolved in 100% DMSO is added. The compounds are mixed and pre-incubated with the enzyme for 10 min at room temperature.

The FL-GMP conversion reaction is initiated by combining 4 parts enzyme and inhibitor mix with 1 part substrate solution (0.225 μL) in a 384-well microtiter plate. The reaction is incubated in dark at room temperature for 15 min. The reaction is halted by addition of 60 μL of binding reagent (1:400 dilution of IMAP beads in binding buffer supplemented with 1:1800 dilution of antifoam) to each well of the 384-well plate. The plate is incubated at room temperature for 1 hour to allow IMAP binding to proceed to completion, and then placed in an Envision multimode microplate reader (PerkinElmer, Shelton, Conn.) to measure the fluorescence polarization (mp).

A decrease in GMP concentration, measured as decreased mp, is indicative of inhibition of PDE activity. $IC_{50}$ values are determined by measuring enzyme activity in the presence of 8 to 16 concentrations of compound ranging from 0.0037 nM to 80,000 nM and then plotting drug concentration versus AmP, which allows $IC_{50}$ values to be estimated using nonlinear regression software (XLFit; IDBS, Cambridge, Mass.)

Various compounds of Examples 1-9 demonstrate good selectivity for PDE1, and can inhibit PDE1 at $IC_{50}$ values equal to or less than 50 nM in the present assay.

Example 11

A selective PDE1 inhibitor of the present invention demonstrates microsomal stability in human microsomal stability assays. The aforementioned selective PDE1 inhibitor demonstrates a K value less than 0.01, and demonstrates a half-life of T½ of about 100-1800 minutes.

Example 12

A selective PDE1 inhibitor of the present invention demonstrates the ability to cross the blood-brain barrier. Following an injection of 10 mg/kg in a suitable mouse model, the aforementioned selective PDE1 inhibitor is detectable at about 3 μM less than about 0.5 hours following the injection.

What is claimed:

1. A compound of Formula V

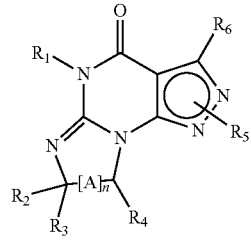

Formula V wherein
(i) $R_1$ is $C_{1-4}$ alkyl;
(ii) $R_4$ is H and $R_2$ and $R_3$ are, independently, H or $C_{1-4}$ alkyl;
(iii) $R_5$ is attached to one of the nitrogens on the pyrazolo portion of Formula V and is a moiety of Formula A

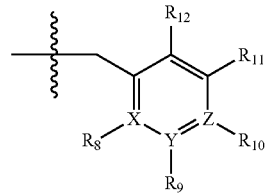

Formula A wherein X, Y and Z are C, and $R_8$, $R_9$, $R_{11}$ and $R_{12}$ are H, and $R_{10}$ is halogen, or heteroaryl optionally substituted with halogen, alkyl, haloalkyl, hydroxy or carboxy; and
(iv) $R_6$ is H, $C_{1-4}$alkyl, arylamino optionally substituted with $C_{1-4}$alkyl or halogen; and
(v) n=0;
in free or pharmaceutically acceptable salt form; provided that
when $R_{10}$ is halogen or unsubstituted heteroaryl, then $R_6$ is arylamino substituted with $C_{1-4}$ alkyl or halogen.

2. A compound according to claim 1, wherein $R_1$ is methyl.

3. A compound according to claim 1, wherein $R_2$ and $R_3$ are $C_{1-4}$ alkyl.

4. A compound according to claim 1, wherein $R_2$ and $R_3$ are both methyl.

5. A compound according to claim 1, wherein $R_{10}$ is heteroaryl optionally substituted with halogen.

6. A compound according to claim 1, wherein $R_{10}$ is pyrid-2-yl.

7. A compound according to claim 1, wherein $R_{10}$ is 5-fluoro-pyrid-2-yl.

8. A compound according to claim 1, wherein $R_{10}$ is 6-fluoro-pyrid-2-yl.

9. A compound according to claim 1, wherein $R_6$ is $C_{1-4}$alkyl.

10. A compound according to claim 1, wherein $R_6$ is ethyl.

11. A compound according to claim 1, wherein $R_6$ is propyl.

12. A compound according to claim 1, wherein $R_6$ is arylamino optionally substituted with $C_{1-4}$alkyl or halogen.

13. A compound according to claim 1, wherein $R_6$ is 4-fluorophenylamino.

14. A compound according to claim 1, wherein the compound is selected from:

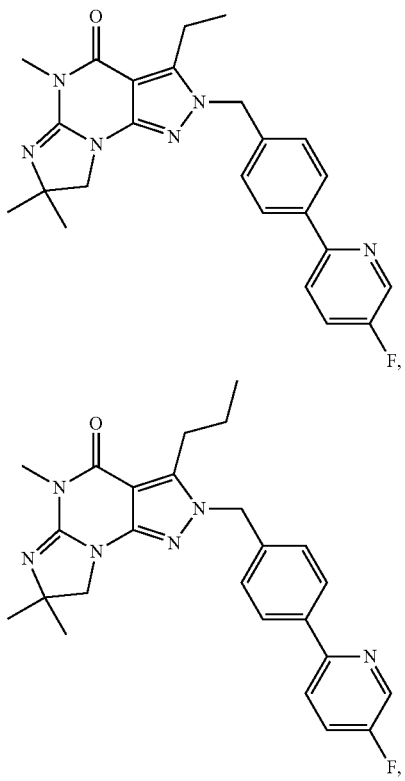

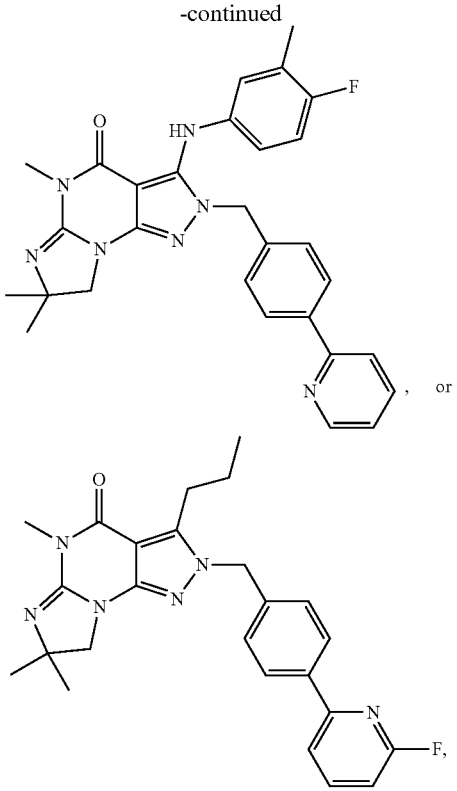

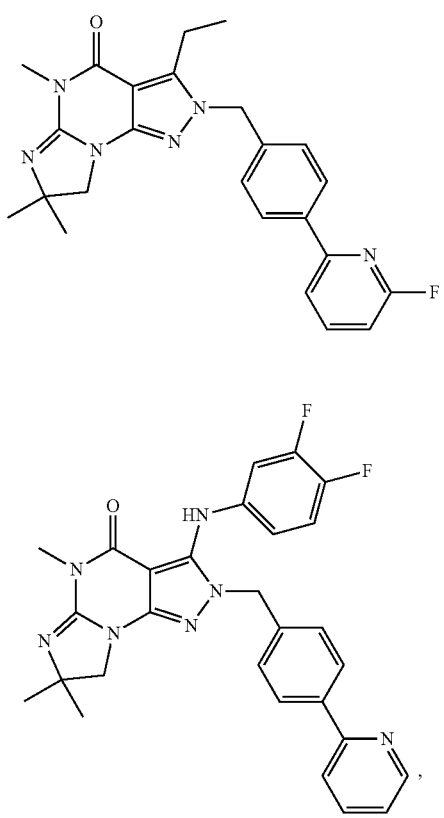

in free or pharmaceutically acceptable salt form.

15. A compound according to claim 1, wherein the compound is selected from:

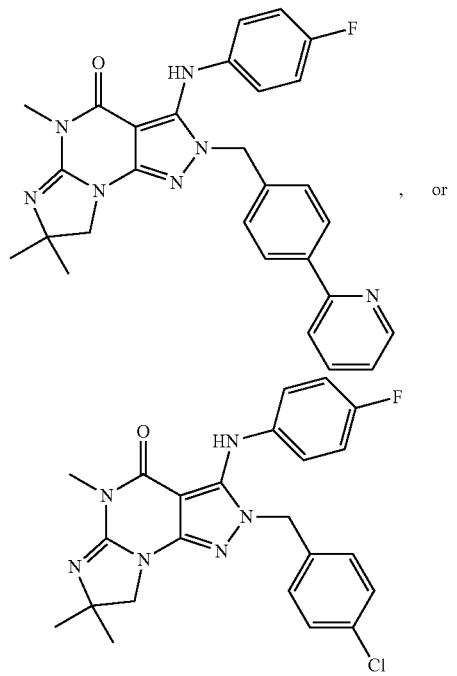

in free or pharmaceutically acceptable salt form.

16. A pharmaceutical composition comprising a compound according to claim 1 in admixture with at least one pharmaceutically acceptable carrier or excipient.

17. A method for the treatment of a CNS disease, disorder, and/or injury, wherein the method comprises the administration of an effective amount of a PDE1 inhibitor to a subject, wherein the administration of the PDE1 inhibitor modulates the subject's level of intracellular cAMP, wherein the PDE1 inhibitor is a compound according to claim 1.

18. A method according to claim 17, wherein the CNS disease, disorder, or injury is a spinal cord injury.

19. The method according to claim 17, wherein the CNS disease, disorder, or injury relates to motor neuron trauma.

20. The method according to claim 17, wherein the CNS disease, disorder, or injury is selected from the group consisting of: neurological traumas and injuries, surgery related trauma and/or injury, retinal injury and trauma, injury related to epilepsy, spinal cord injury, brain injury, brain surgery, trauma related brain injury, trauma related to spinal cord injury, brain injury related to cancer treatment, spinal cord injury related to cancer treatment, brain injury related to infection, brain injury related to inflammation, spinal cord injury related to infection, spinal cord injury related to inflammation, brain injury related to environmental toxins, and spinal cord injury related to environmental toxins.

21. The method according to claim 17, wherein the CNS disease, disorder, or injury is a neurodegenerative disorder.

22. The method according to claim 21, wherein the neurodegenerative disease, disorder, or injury is selected from the group consisting of: Alzheimer's disease, Multiple Sclerosis, Glaucoma, Frontotemporal dementia, Dementia with Lewy bodies, Corticobasal degeneration, Progressive supranuclear palsy, Prion disorders, Huntington's disease, Multiple system atrophy, Parkinson's disease, Amyotrophic lateral sclerosis, Hereditary spastic paraparesis, Spinocerebellar atrophies, Friedreich's ataxia, Amyloidoses, Metabolic (diabetes) related disorders, Toxin related disorders, chronic CNS inflammation, and Charcot Marie Tooth disease.

23. A method of treatment or prophylaxis of a PNS disease, disorder, or injury, wherein the method comprises administration of an effective amount of a PDE1 inhibitor to a subject in order to increase the subject's intracellular levels of cAMP, wherein the PDE1 inhibitor is a compound according to claim 1.

24. A method according to claim 17, wherein the PDE1 inhibitor is administered to a patient that is shown to have elevated intracellular calcium levels compared to a control subject.

25. A compound according to claim 1, wherein $R_{10}$ is halogen and $R_6$ is arylamino substituted with $C_{1-4}$ alkyl or halogen.

26. A compound according to claim 1, wherein $R_{10}$ is unsubstituted heteroaryl and $R_6$ is arylamino substituted with $C_{1-4}$ alkyl or halogen.

27. A compound according to claim 1, wherein $R_{10}$ is heteroaryl substituted with halogen, alkyl, haloalkyl, hydroxy.

28. A compound according to claim 27, wherein $R_6$ is $C_{1-4}$ alkyl.

* * * * *